US008686052B2

(12) United States Patent
Niitsu et al.

(10) Patent No.: US 8,686,052 B2
(45) Date of Patent: Apr. 1, 2014

(54) TARGETING AGENT FOR CANCER CELL OR CANCER-ASSOCIATED FIBROBLAST

(75) Inventors: Yoshiro Niitsu, Sapporo (JP); Rishu Takimoto, Sapporo (JP)

(73) Assignee: Nitto Denko Corporation, Ibaraki, Osaka (JP)

( * ) Notice: Subject to any disclaimer, the term of this patent is extended or adjusted under 35 U.S.C. 154(b) by 865 days.

(21) Appl. No.: 12/450,571

(22) PCT Filed: Mar. 28, 2008

(86) PCT No.: PCT/JP2008/056735
§ 371 (c)(1),
(2), (4) Date: Feb. 22, 2010

(87) PCT Pub. No.: WO2008/120815
PCT Pub. Date: Oct. 9, 2008

(65) Prior Publication Data
US 2010/0144659 A1    Jun. 10, 2010

(30) Foreign Application Priority Data

| Mar. 30, 2007 | (JP) | 2007-091808 |
| Oct. 4, 2007 | (JP) | 2007-261202 |
| Dec. 17, 2007 | (JP) | 2007-324459 |

(51) Int. Cl.
| *A01N 31/04* | (2006.01) |
| *A61K 31/07* | (2006.01) |
| *C12N 15/11* | (2006.01) |
| *C07C 35/18* | (2006.01) |
| *A61K 9/127* | (2006.01) |
| *A61K 48/00* | (2006.01) |
| *C12N 15/113* | (2010.01) |

(52) U.S. Cl.
CPC ............ *A61K 31/07* (2013.01); *A61K 2300/00* (2013.01); *A61K 9/127* (2013.01); *A61K 48/005* (2013.01); *C12N 15/113* (2013.01); *C12N 2310/14* (2013.01); *C12N 2320/32* (2013.01)
USPC .......................... 514/725; 514/44 A; 568/824

(58) Field of Classification Search
CPC . A61K 2300/00; A61K 9/127; A61K 9/0019; A61K 31/713; C12N 15/111; C12N 15/113; C12N 2310/14; C12N 2320/32
USPC ................... 514/725, 44 A; 568/824
See application file for complete search history.

(56) References Cited

U.S. PATENT DOCUMENTS

| 5,472,954 A | 12/1995 | Loftsson |
| 5,534,261 A | 7/1996 | Rodgers et al. |
| 5,583,020 A | 12/1996 | Sullivan |
| 5,668,117 A | 9/1997 | Shapiro |
| 5,733,572 A | 3/1998 | Unger et al. |
| 5,753,261 A | 5/1998 | Fernandez et al. |
| 5,785,976 A | 7/1998 | Westesen et al. |
| 5,811,119 A | 9/1998 | Mehta et al. |
| 5,820,879 A | 10/1998 | Fernandez et al. |
| 5,942,230 A | 8/1999 | Wu et al. |
| 6,037,481 A | 3/2000 | Zucchetti et al. |
| 6,071,495 A | 6/2000 | Unger et al. |
| 6,159,591 A | 12/2000 | Beihoffer et al. |
| 6,177,274 B1 | 1/2001 | Park et al. |
| 6,187,315 B1 | 2/2001 | Falcon |
| 6,214,345 B1 | 4/2001 | Firestone et al. |
| 6,217,912 B1 | 4/2001 | Park et al. |
| 6,238,917 B1 | 5/2001 | Hendry et al. |
| 6,248,363 B1 | 6/2001 | Patel et al. |
| 6,251,428 B1 | 6/2001 | Yoo |
| 6,328,988 B1 | 12/2001 | Uhrich |
| 6,342,219 B1 | 1/2002 | Thorpe |
| 6,342,221 B1 | 1/2002 | Thorpe et al. |
| 6,344,206 B1 | 2/2002 | Nguyen et al. |
| 6,379,683 B1 | 4/2002 | Simonnet et al. |
| 6,441,025 B2 | 8/2002 | Li et al. |
| 6,471,968 B1 | 10/2002 | Baker, Jr. et al. |
| 6,472,507 B1 | 10/2002 | Fischer et al. |
| 6,524,583 B1 | 2/2003 | Thorpe et al. |
| 6,586,524 B2 | 7/2003 | Sagara |
| 6,610,841 B1 | 8/2003 | Warren |
| 6,645,528 B1 | 11/2003 | Straub et al. |
| 6,652,886 B2 | 11/2003 | Ahn et al. |
| 6,656,734 B1 | 12/2003 | Bischoff et al. |

(Continued)

FOREIGN PATENT DOCUMENTS

| CN | 1917859 A | 2/2007 |
| CN | 101102795 A | 1/2008 |
| EP | 0932399 | 8/1999 |
| EP | 1698329 | 9/2006 |
| EP | 1842557 | 10/2007 |
| EP | 2135600 | 12/2009 |
| EP | 2 258 395 A1 | 12/2010 |
| JP | H02-502094 | 7/1990 |
| JP | 5-503076 | 5/1993 |
| JP | 8-002799 | 1/1996 |

(Continued)

OTHER PUBLICATIONS

Dillard et al. Molecular Carcinogenesis, Apr. 2007, vol. 46, pp. 315-329.*
Devi, GR. Cancer Gene Therapy, 2006, vol. 13, pp. 819-829.*
Park et al. Cancer Research, Available online Nov. 2005, vol. 65, pp. 9923-9933.*

(Continued)

*Primary Examiner* — Samira Jean-Louis
(74) *Attorney, Agent, or Firm* — Knobbe Martens Olson & Bear LLP

(57) ABSTRACT

Disclosed are a novel therapeutic agent and a novel treatment method for cancer. Specifically disclosed are: a targeting agent for a cell selected from the group consisting of a cancer cell and a cancer-associated fibroblast, which comprises a retinoid; a substance delivery carrier for the cell, which comprises the targeting agent; an anti-cancer composition utilizing the targeting agent or the carrier; an anti cancer-associated fibroblast composition; and a method for treatment of cancer.

5 Claims, 23 Drawing Sheets
(18 of 23 Drawing Sheet(s) Filed in Color)

(56) References Cited

U.S. PATENT DOCUMENTS

| | | |
|---|---|---|
| 6,676,941 B2 | 1/2004 | Thorpe et al. |
| 6,680,047 B2 | 1/2004 | Klaveness et al. |
| 6,696,038 B1 | 2/2004 | Mahato et al. |
| 6,730,334 B2 | 5/2004 | Zhao |
| 6,740,336 B2 | 5/2004 | Trubetskoy et al. |
| 6,746,678 B1 | 6/2004 | Shapiro |
| 6,764,698 B1 | 7/2004 | Byun et al. |
| 6,838,528 B2 | 1/2005 | Zhao |
| 6,896,890 B2 | 5/2005 | Singh et al. |
| 6,908,626 B2 | 6/2005 | Cooper et al. |
| 6,994,862 B2 | 2/2006 | Jeong et al. |
| 6,998,115 B2 | 2/2006 | Langer et al. |
| 7,018,655 B2 | 3/2006 | Lele et al. |
| 7,045,356 B2 | 5/2006 | Trubetskoy et al. |
| 7,060,498 B1 | 6/2006 | Wang |
| 7,064,127 B2 | 6/2006 | Friedman et al. |
| 7,071,163 B2 | 7/2006 | Sokoloff et al. |
| 7,074,389 B2 | 7/2006 | Frankenberger et al. |
| 7,098,030 B2 | 8/2006 | Rozema et al. |
| 7,101,576 B2 | 9/2006 | Hovey et al. |
| 7,101,995 B2 | 9/2006 | Lewis et al. |
| 7,122,202 B2 | 10/2006 | Allen et al. |
| 7,196,145 B2 | 3/2007 | Ignacious |
| 7,223,724 B1 | 5/2007 | Alderson et al. |
| 7,223,837 B2 | 5/2007 | De Groot et al. |
| 7,262,221 B2 | 8/2007 | Uhrich et al. |
| 7,265,186 B2 | 9/2007 | Zhao |
| 7,276,249 B2 | 10/2007 | Ryde et al. |
| 7,276,348 B2 | 10/2007 | Glick |
| 7,297,515 B1 | 11/2007 | Szankasi et al. |
| 7,297,786 B2 | 11/2007 | McCray et al. |
| 7,316,811 B2 | 1/2008 | Zhao et al. |
| 7,320,802 B2 | 1/2008 | Ryde et al. |
| 7,358,223 B2 | 4/2008 | Zhao et al. |
| 7,404,969 B2 | 7/2008 | Chen et al. |
| 7,700,541 B2 | 4/2010 | Tanaka et al. |
| 7,700,542 B2 | 4/2010 | Zhao et al. |
| 8,003,621 B2 | 8/2011 | Niitsu et al. |
| 8,173,170 B2 | 5/2012 | Niitsu et al. |
| 8,178,124 B2 | 5/2012 | Niitsu et al. |
| 8,258,235 B2 | 9/2012 | Zhao et al. |
| 2002/0012998 A1 | 1/2002 | Gonda et al. |
| 2002/0026060 A1 | 2/2002 | Belloni et al. |
| 2002/0041898 A1 | 4/2002 | Unger et al. |
| 2002/0143062 A1 | 10/2002 | Lopez-Berestein et al. |
| 2003/0064094 A1 | 4/2003 | Frankenberger et al. |
| 2003/0073619 A1 | 4/2003 | Mahato et al. |
| 2003/0096739 A1 | 5/2003 | Morris |
| 2003/0147958 A1 | 8/2003 | Ahn et al. |
| 2003/0161791 A1 | 8/2003 | Bentley et al. |
| 2003/0211143 A1 | 11/2003 | Liu et al. |
| 2003/0215395 A1 | 11/2003 | Yu et al. |
| 2004/0071654 A1 | 4/2004 | Anderson et al. |
| 2004/0106125 A1 | 6/2004 | Duggan et al. |
| 2004/0138154 A1 | 7/2004 | Yu et al. |
| 2004/0142474 A1 | 7/2004 | Mahato et al. |
| 2005/0002999 A1* | 1/2005 | Mehta et al. .................. 424/450 |
| 2005/0004064 A1 | 1/2005 | Tei et al. |
| 2005/0153337 A1 | 7/2005 | Manoharan |
| 2005/0165227 A1 | 7/2005 | Vlahov et al. |
| 2005/0220859 A1 | 10/2005 | Frankenberger et al. |
| 2005/0256051 A1 | 11/2005 | Morris |
| 2005/0265961 A1 | 12/2005 | Langer et al. |
| 2006/0093674 A1 | 5/2006 | Slobodkin et al. |
| 2006/0127482 A1 | 6/2006 | Fewell et al. |
| 2006/0147376 A1 | 7/2006 | Yu et al. |
| 2006/0258751 A1 | 11/2006 | Zhao et al. |
| 2007/0020761 A1 | 1/2007 | Yu et al. |
| 2007/0072171 A1 | 3/2007 | Yu et al. |
| 2007/0243157 A1 | 10/2007 | Tanaka et al. |
| 2008/0014253 A1 | 1/2008 | Jorgensen et al. |
| 2008/0145338 A1 | 6/2008 | Anderson et al. |
| 2008/0193512 A1 | 8/2008 | Niitsu et al. |
| 2008/0207553 A1 | 8/2008 | Zhao et al. |
| 2008/0220056 A1 | 9/2008 | Arthur et al. |
| 2008/0312174 A1 | 12/2008 | Yu et al. |
| 2009/0105179 A1 | 4/2009 | Yu et al. |
| 2010/0028416 A1 | 2/2010 | Yu et al. |
| 2010/0144659 A1 | 6/2010 | Niitsu et al. |
| 2010/0210715 A1 | 8/2010 | Zhao et al. |
| 2011/0104255 A1 | 5/2011 | Niitsu et al. |
| 2011/0229558 A1 | 9/2011 | Niitsu et al. |
| 2011/0257249 A1 | 10/2011 | Niitsu et al. |
| 2012/0076852 A1 | 3/2012 | Niitsu |
| 2012/0189691 A1 | 7/2012 | Niitsu |
| 2012/0269886 A1 | 10/2012 | Niitsu |

FOREIGN PATENT DOCUMENTS

| | | |
|---|---|---|
| JP | 8-268906 A1 | 10/1996 |
| JP | 11-269076 | 10/1999 |
| JP | 2002-47211 | 2/2002 |
| JP | 2002-363094 | 12/2002 |
| JP | 2002-371006 A1 | 12/2002 |
| JP | 2003-219893 A | 8/2003 |
| JP | 2003-528055 A | 9/2003 |
| JP | 2003-528131 | 9/2003 |
| JP | 2004-083436 A | 3/2004 |
| JP | 2004-523236 | 8/2004 |
| JP | 2004-524371 A | 8/2004 |
| JP | 2005-531564 A | 10/2005 |
| JP | 2005-531628 A1 | 10/2005 |
| JP | 2005-532050 | 10/2005 |
| JP | 2006-506071 | 2/2006 |
| JP | 2006-522158 A | 9/2006 |
| JP | 2007-529197 A | 10/2007 |
| JP | 4533420 | 6/2010 |
| WO | WO 88/06883 | 9/1988 |
| WO | WO 91/04748 | 4/1991 |
| WO | WO 97/33618 | 9/1997 |
| WO | WO 00/64478 | 11/2000 |
| WO | WO 01/68081 | 9/2001 |
| WO | WO 01/72283 | 10/2001 |
| WO | WO 02/28387 | 4/2002 |
| WO | WO 02/32413 | 4/2002 |
| WO | WO 02/066646 | 8/2002 |
| WO | WO 02/083186 A1 | 10/2002 |
| WO | WO 02/092600 | 11/2002 |
| WO | WO 03/009881 | 2/2003 |
| WO | WO 03/080594 A1 | 10/2003 |
| WO | WO 03/97107 | 11/2003 |
| WO | WO 03/097647 | 11/2003 |
| WO | WO 2004/001381 A2 | 12/2003 |
| WO | WO 2004/002489 | 1/2004 |
| WO | WO 2004/019921 | 3/2004 |
| WO | WO 2004/043239 A2 | 5/2004 |
| WO | WO 2004/065636 | 8/2004 |
| WO | WO 2004/069159 | 8/2004 |
| WO | WO 2005/028498 A2 | 3/2005 |
| WO | WO 2005/082402 | 9/2005 |
| WO | WO 2006/041617 | 4/2006 |
| WO | WO 2006/066001 | 6/2006 |
| WO | WO 2006/068232 A1 | 6/2006 |
| WO | WO 2007/028154 | 3/2007 |
| WO | WO 2007/067417 | 6/2007 |
| WO | WO 2007/104946 | 9/2007 |
| WO | WO 2007/120479 | 10/2007 |
| WO | WO 2008/006583 | 1/2008 |
| WO | WO 2008/120815 | 10/2008 |
| WO | WO 2008/151150 | 12/2008 |
| WO | WO 2009/036368 | 3/2009 |
| WO | WO 2009/116257 | 9/2009 |
| WO | WO 2010/014117 | 2/2010 |
| WO | WO 2010/026766 | 3/2010 |
| WO | WO 2010/029760 | 3/2010 |

OTHER PUBLICATIONS

Calderwood et al. Trends in Biochemical Sciences, 2006, vol. 31, No. 3, pp. 164-172.*
Hendershot et al. Current Biology, 2000, vol. 10, pp. R912-R915.*
Sauk et al. Frontiers in Bioscience, 2005, vol. 10, pgs. 107-118.*
Office Action dated Mar. 9, 2011 for Chinese Application No. 200880010916.8 filed Sep. 29, 2009.

(56) References Cited

OTHER PUBLICATIONS

Camps et al., "Fibroblast-mediated acceleration of human epithelial tumor growth in vivo" *Proc Natl Acad Sci USA* (1990) 87(1):75-9.
Micke et al., "Exploring the tumour environment: cancer-associated fibroblasts as targets in cancer therapy" *Expert Opinion* (2005) 9(6):1217-3.
Nastruzzi et al., "Liposome-associated retinoic acid increased in vitro antiproliferative effects on neoplastic cells" *FEBS Letters* (1990) 259(2):293-296.
Olumi et al., "Carcinoma-associated fibroblasts direct tumor progression of initiated human prostatic epithelium" *Cancer Research* (1999) 59(19):5002-11.
Torchilin, V.P., "Targeted pharmaceutical nanocarriers for cancer therapy and imaging" *The AAPS Journal* (2007) 9(2):E128-47.
International Preliminary Report on Patentability issued Oct. 15, 2009 in PCT/JP2008/056735, filed Mar. 28, 2008.
International Preliminary Report on Patentability and Written Opinion issued Oct. 22, 2009 in PCT/JP2008/056735, filed Mar. 28, 2008.
Patent Examination Report No. 1, Jul. 27, 2012 for Australian Application No. 2008233550.
Office Action issued on Aug. 14, 2012 for Japanese Application No. 2009-507561.
Choi et al., "Inhibition of tumor growth by biodegradable microspheres containing all-*trans*-retinoic acid in a human head-and-neck cancer xenograft," Int. J. Cancer: 107, 145-148 (2003).
Goldberg et al., "Phase I trial of interferon α2b and liposome-encapsulated all-*trans*retinoic acid in the treatment of patients with advanced renal cell carcinoma," Cancer, vol. 95, No. 5, pp. 1220-1227 Sep. 15, 2002.
Brash, E. D. and Havre, P. A., "New careers for antioxidants," *Proceedings of the National Academy of Sciences*, (Oct. 2002) 99(22): 13969-13971.
Saito, M. et al., "Cytotoxicity and apoptosis induction by butylated hydroxyanisole (BHA) and butylated hydroxytoluene (BHT)," *Anticancer Res.* (2003) 23(6C): 4693-4701.
Sakagami, H. et al., "Apoptpsis-inducing activity of vitamin C and vitamin K," *Cell Mol. Biol (Noisy-le-grand)* (Feb. 2000) 46(1): 129-143.
Sigounas, G. et al., "dl-alpha-Tocopherol induces apoptosis in erythroleukemia, prostate, and breast cancer cells," *Nutrition and Cancer*, (1997) 28(1): 30-35.
Szondy, Z. et al., "Induction of apoptosis by retinoids and retinoic acid receptorg-selective compounds in mouse thymocytes through a novel apoptosis pathway," *Molecular Pharmacology* (1997) 51: 972-982.
Agrawal et al., "Antisense therapeutics: Is it as simple as complimentary base recognition?" *Molecular Med. Today* (2000) 6: 72-81.
Beljaars et al., "Albumin modified with mannosa 6-phosphate: a potential carrier for selective delivery of antifibrotic drugs to rat and human hepatic stellate cells," *Hepatology*, (1999):29(5):1486-1493.
Benedetti, A. et al., "Inhibition of the Na+/H+ exchanger reduces rat hepatic stellate cell activity and liver fibrosis: an in vitro and in vivo study," *Gastroenterology* (2001)120(2):545-56.
Blomhoff, R. et al., "Newly administered [$^3$H] retinol is transferred from hepatocytes to stellate cells in liver for storage," *Experimental Cell Research* (1984) 150:186-193.
Blomhoff, R. et al., "Hepatic uptake of [$^3$H] retinol bound to the serum retinol binding protein involves both parenchymal and perisinusoidal stellate cells," *The Journal of Biological Chemistry* (1985) 260(25): 13571-13575.
Chansri, N. et al., "Inhibition of liver metastasis by all-*trans* retinoic acid incorporated into O/W emulsions in mice," *International Journal of Pharmaceutics* (2006) 321:42-49.
Chirila et al., "The use of synthetic polymers for delivery of therapeutic antisense oligodeoxypucleotides," *Biomaterials* (2002) 23: 321-342.
Clark, et al. "Cationic lipid-mediated gene transfer: Current concepts," *Curr. Opin. Mol. Ther.*. (Apr. 1999) 1(2): 158-176.
Crooke, S.T., "Progress in antisense technology," *Annual Review of Medicine* (2004) 55: 61-95.

Devi, G. R., "siRNA-based approaches in cancer therapy," *Cancer Gene Therapy* (2006) 13: 819-829.
Dillard, et al., "Retinol decreases β-catenin protein levels in retinoic acid-resistant colon cancer cell lines," *Molecular Carcinogenesis* (2007) 46:315-329.
Dixon, et al., "*Nonmenclature of retinoids.*" *Pure & AppL Chem.*, (1983) 55(4): 721-726.
Dunham, et al., "Membrane fusion: Studies with a calcium-sensitive dye, arsenazo III, in liposomes," *Proceedings of the National Academy of Science* (Apr. 1977) 74 (4): 1580-1584.
Elbashir, S.M. et al., "Duplexes of 21-nucleotide RNAs mediate RNA interference in cultured mammalian cells," *Nature* (2001) 411:494-498.
Ermak et al., "Monoclonal antibody-directed targeting of fluorescent polystyrene microspheres to Peyer's patch M cells," *Immunology* (1991) 73: 227-280.
Fallowfield, I. A. et al., "Targeted treatment for cirrhosis," *Expert Opin. Ther. Targets* (Oct .2004) 8(5):423-35.
Fingl, et al., The pharmacological basis of therapeutics, Fifth Edition, MacMillan Publishing Co, (1975) Cover and contents pages only.
Fire, A. et al., "Potent and specific genetic interference by double-stranded RNA in *Caenorhabditis elegans*," *Nature* (1998) 391:806-811.
Fortuna, V.A. et al., "Hepatic stellate cells uptake of retinol associated with retinol-binding protein or with bovine serum albumin," *Journal of Cellular Biochemistry* (2003) 90(4):792-805.
Fortunati, et al., "A multi-domain protein for β1 integrin-targeted DNA delivery," *Gene Therapy* (2000) 7:1505- 1515.
Friedman, S. L., "Targeting siRNA to arrest fibrosis," *Nature Biotechnology* (Apr. 2008) 26(4): 399-400.
Fuja, T.J. et al., "Trans differentiation of vocal-fold stellate cells and all-trans retinol-induced deactivation," *Cell Tissue Res* (2005) 322(3):417-24.
George, J. et al., "In vivo inhibition of rat stellate cell activation by soluble transforming growth factor p type II receptor: A potential new therapy for hepatic fibrosis," *Proc. Nat. Acad. Sci. USA* (Oct. 1999) 96(22):12719-24.
Greene et al, "Protective groups in organic synthesis," John Wiley & Sons, 3rd Edition (1999).
Hagiwara, S. et al., "Inhibition of type I procollagen production by tRA va CTE-HSP 47 ribozyme," *J Gene Med*. (2003) 5:784-94.
Hazen, G.G., "the synthesis of nitrogen mustard derivatives of some steroids and related compounds," Dissertation submitted for the degree of Doctor of Philosophy in the University of Michigan, Abstracts (1951) 12(4): 449.
Houglum, et al., "Two different cis-acting regulatory regions direct cell-specific transcription of the collagen a1 (1) gene in hepatic stellate cells and in skin and tendon fibroblasts," *J. Clin. Invest*. (1995) 96: 2269-2276.
Hwang, et al., "Phospholipid-based microemulsion formulation of all-*trans*-retinoic acid for parenteral administration," *International Journal of Pharmaceutics* (2004) 276:175-183.
Iimuro, Y. et al., "Delivery of matrix metalloproteinase-1 attenuates established liver fibrosis in the rat," *Gastroenterology* (2003) 124:445-458.
International Search Report and Written Opinion dated May 27, 2008 for International Application No. PCT/JP2008/056735, filed Mar. 28, 2008.
Jaster, R., "Molecular regulation of pancreatic stellate cell function," *Molecular Cancer* (Oct. 2004) 3(1):26.
Jeong, et al., "Polyion complex micelles composed of all-trans retinoic acid and poly (ethylene glycol)-grafted-chitosan," *Journal of Pharmaceutical Sciences* (Nov. 2006) 95(11): 2348-2360.
Jezequel, A.M. et al., "A morphological study of the early stages of hepatic fibrosis induced by low doses of dimentylnitrosame in the rat," *J. Hepatol*. (Oct. 1987) 5(2): 174-81.
Kamps, J.A.A.M. et al., "Massive targeting ofliposomes, surface-modified with anionized albumins, to hepatic endothelial cells," *Proceedings of the National Academy of Sciences USA* (1997) 94(21):11681-11685.
Kang et al., "Mannose-6 phosphateyinsulin-like growth factor-II receptor is a receptor for retinoic acid," *Proc. Natl. Acad. Sci*. (1998) 95: 13671-13676.

(56) References Cited

OTHER PUBLICATIONS

Kikuchi, H., "Liposomes based on nanotechnology. Past, present and future. Part II," *Pharm Tech Japan*(2003) 19(3):419-433.
Kim, et al., "Folate-tethered emulsion for the target delivery of retinoids to cancer cells." *European Journal of Pharmaceutics and Biopharmaceutics* (2008) 68:618-625.
Kim, et al., "Efficient siRNA delivery using water soluble lipopolymer for anti-angiogenic gene therapy," *J. Controlled Release* (2007) 357-363.
Kim, et al., "Retinol-encapsulated low molecular water-soluble chitosan nanoparticles," *International Journal of Pharmaceutics* (Aug. 2006) 319:130-138.
Kircheis, et al., "Tumor targeting with surface-shielded ligand-polycation DNA complexes." *Journal of Controlled Release* (2001) 72:165-170.
Landen, et al., *Cancer Res.* (Aug. 2005) 65(15):6911.
Li, et al., "Transferrin/Transferrin receptor-mediated drug delivery," *Medicinal Research Reviews* (2002) 22(3):225- 253.
Liu, W.B. et al, "Inhibition on the production of collagen type I, III of activated hepatic stellate cells by antisense TIMP-1 recombinant plasmid," *World J. Gastroenterol* (Feb. 2003) 9(2):316-9.
Liébecq, "Biochemical nomenclature and related documents," 2nd Ed. Portland Press (1992): 247-251.
Lim, et al., "Formulation parameters determining the physicochemical characteristics of solid lipid nanoparticles loaded with all-trans retinoic acid," *International Journal of Pharmaceutics* (2002) 243:135-146.
Liu, X.J. et al., "Effects of the tyrosine protein kinase inhibitor genistein on the proliferation, activation of cultured rat hepatic stellate cells," *World J. Gastroenterology*. (Aug. 2002) 8(4):739-45.
Lynn, et al., "Accelerated discovery of synthetic transfection vectors: Parallel synthesis and screening of a degradable polymer," *Journal of the American Chemical Society* (2001) 123: 8155-8156.
Ma, et al., "Comparison of stability for all-*trans* retinoic acid nanosuspensions and lipid nanoparticle formulations," *International Conference on Complex Medical Engineering* (2007) 197-202.
Madro, A. et al., "The role of pancreatic stellate cells and cytokines in the development of chronic pancreatitis," *Med. Sci. Monit.* (2004) 10(7): RA166-70.
March, "Advanced Organic Chemistry," 3rd Edition (1985) 711-12.
Marcucci, et al., "Active targeting with particulate drug carriers in tumor therapy: fundamentals and recent progress," *Drug Discovery Today* (2004) 9(5):219-228.
Marra, F. et al., "Ligands of peroxisome proliferator-activated receptor y modulate profibrogenic and pro inflammatory actions in hepatic stellate cells," *Gastroenterology* (Aug. 2000) 119(2):466-78.
Massaro, et al., "Noninvasive delivery of small inhibitory RNA and other reagents to pulmonary alveoli in mice," *Am J Physiol Long Cell Mol Physiol* (2004) 287: 1066-1070.
McCAFFERY, et al., "RNA interference in adult mice," *Nature* (Jul. 2002) 418(6893):38-39.
Miao, et al., "Heat shock protein 47 and pulmonary fibrosis", *International J. Respiration* (2007) 27(22):1745-1747.
Moss, "Biochemical Nomenclature and Related Documents," Portland Press, 2nd Edition (1992) 247-251.
Noa N., "Retinoid-binding proteins: Mediators of retinoid action," *Biochem J.* (2000) 248: 481-495.
Opalinska et al., "Nucleic-acid therapeutics: Basic principles and recent applications," *Nature Rev.* (2002) 1: 503-514.
Orr, I.G. et al., "Mechanism of action of the antifibrogenic compound gliotoxin in rat liver cells," *Hepatology* (Jul. 2004) 40(1):232-42.
Pappo, et al., "Monoclonal antibody-directed targeting of fluorescent polystyrene microspheres to Peyer's patch M cells." *Immunology* (1991) 73:277-280.
Park, et al., "Retinol inhibits the growth of *all-trans*-retinoic acid-sensitive and *all-trans*-retinoic acid-resistant colon cancer cells through a retinoic acid receptor-independent mechanism," *Cancer Res.* (Nov. 2005) 65:9923-9933.
Peracchi, et al., "Prospects for antiviral ribozymes and deoxyribozymes," *Rev. Med. Virolo.* (2004) 14: 47-64.

Peterkofsky, et al., "Use of a mixture of proteinase-free collagenases for the specific assay of radioactive collagen in the presence of other proteins," *Biochemistry* (Mar. 1971) 10(6):988- 94.
Pinzani, M. et al., "Liver fibrosis: From the bench to clinical targets," *Dig. Liver Dis.* (Apr. 2004) 36(4):231-42.
Qi, Z. et al., "Blockade of type p transforming growth factor signaling prevents liver fibrosis and dysfunction in the rat," *Proc. Natl. Acad. Sci. USA* (Mar. 1999) 96(5):2345-9.
"Remington's Pharmaceutical Sciences," 18th Edition, Mack Publishing Company (1990).
Vogel, S., et al., "An imortalized rat liver stellate cell line (HSC-T6): a new cell model for the study of retinoid metabolism in vitro." Journal of Lipid Research, ( 2000) 41: 882-893.
Sakaida et al., "Fibrosis Accelerates the Development of Enzyme-Altered Lesions in the Rat Liver," *Hepatology* Nov. 1998; 28:1247-1252.
Sasaki, H. et al., "Induction of heat shock protein 47 synthesis by TGF-p and IL-1P via enhancement of the heat shock element binding activity of heat shock transcription factor 1," *The Journal of Immunology* (2002)168:5178-5183.
Sato, et al, "Resolution of liver cirrhosis using vitamin A-coupled liposomes to deliver siRNA against a collagen-specific chaperone," *Nature Biotechnology* (2008) 26(4):431-442.
Senoo, et al., "Hepatic stellate cells and alveolar septal cells," Respiration (1997) 16(4): 604-615.
Senoo, "Studies of the vitamin A-storing (stellate) cell system-from molecules to the arctic area," *Vitamins*, Japan (2006) 80(3): 105-113.
Singh et al', "Liposome encapsulated vitamin A compounds exhibit greater stability and diminished toxicity," *Biophysical Chemistry* (1998) 73: 155-162.
Sioud, M. et al., "Cationic Liposome-mediated delivery of siRNAs in adult mice," *Biochem Biophys Res Commun* (Dec. 26, 2003) 312(4):1221.
Socaciu, et al., "Different ways to insert carotenoids into liposomes affect structure and dynamics of the bilayer differently," *Biophysical Chemistry* (2002) 99: 1-15.
Sun, et al., "Retinoids and their receptors in cancer development and chemoprevention," *Crit. Rev. Onco/Hemato.* (2002) 41: 41-55.
Tabata, et al., "All-trans-retinoic acid prevents radiation- or bleomycin-induced pulmonary fibrosis", *Am J Respir Crit Care Med.* (Dec. 15, 2006) 174(12):1352-60.
Tagami et al., "The gene-slicing effect of siRNA in cationic lipoplexes is enhanced by incorporating pDNA in the complex," *Intl. J Pharmaceutics* (Oct. 2006) 333: 62-69.
Takahashi, et al., "Effects on M5076-heptatic metastasis of retinoic acid and *n*-(4-hydroxphenyl)retinamide, fenretinide entrapped in sg-liposomes", *Bio. Pharm. Bull.* (2003) 26(7):1060-1063.
Torchilin, V. P. et al., "Immunomicelles: Targeted pharmaceutical carriers for poorly soluble drugs," *PNAS.* (2003) 100(10):6039-6044.
Torchilin, V. P. "Drug Targeting," *European Journal of Pharmaceutical Sciences.* (2000)11(2):81-91.
Ueda et al., "Fibroblasts and their related cells," *Respiration* (1995) 14(7): 708-712.
Ueki, K. et al., "Hepatocyte growth factor gene therapy ofliver cirrhosis in rats," *Nat. Med.* (Feb. 1999) 5(2):226-30.
Ui- Tei, K. et al., "Sensitive assay of RNA interference in *Drosphila* and Chinese hamster cultured cells using firefly luciferase gene as target," *FEBS Letters* (2000) 479:79-82.
Viguera et al., "A water-soluble polylysine-retinalddehyde schiff base," *The Journal of Bilogical Chemistry* (1990) 265(5): 2527-2532.
Wang, L. et al., "Effects of herbal compound 861 on human hepatic stellate cell proliferation and activation," *World J. Gastroenterology* (Oct. 2004) 10(19):2831-2835.
Wassall, et al., "Retinoid-phospholipid Interactions as studied by magnetic resonance," *Bulletin of Magnetic Resonance* (1987) 9(3): 85-89.
Watanabe, et al, "Treatment of idiopathic myelofiosis employing siRNA for heat shock protein 7 (siRNA/HSP47) encapsulated in liposomes," *Blood* (2007) 110: 235.
Whitmer, et al., "Membrane-membrane interactions associated with rapid transfer of liposomal bilirubin to microsomal UDP-glucoronyltransferease," *Biochemical Journal* (1987) 244: 41-47.

(56) References Cited

OTHER PUBLICATIONS

Wu, J. et al., "Modification ofliposomes for liver targeting," *Journal of Hepatology* (1996)24(6):757-763.

Yoshiji, H. et al., "Angiotensin-II type 1 receptor interaction is a major regulator for liver fibrosis development in rats," *Hepatology* (Oct. 2001)34:745-50.

Zhang et al., "Cationic lipids and polymers mediated vectors for delivery of siRNA," *J. Control Release* (2007) 123: 1-10.

Zimmermann, T.S. et al., *Nature* (May 2006) 441(7089):111-14.

Office Action dated Apr. 30, 2013 for India Patent Application No. 1573/MUMNP/2009, filed on Aug. 8, 2009.

Office Action dated Jan. 23, 2013 for Taiwanese Patent Application No. 09111089, filed on Mar. 27, 2008.

Hanamura, N. et al:, "Expression of Fibronectin and Tenascin-C mRNA by Myofibroblasts. Vascular Cells and Epithelial Cells in Human Colon Adenomas and Carcinomas." *Int. J. Cancer* (1997) 73(1):10-15.

Hard, G C. et al, "Ultrastructural Study of the Development of Interstitial Lesions Leading to Mesenchymal Neoplasia Induced in the Rat Renal Cortex by Dimethylnitrosamine," *Cancer Research* (1971) 31(3):337-347.

Hirai K. et al., "Immunohistochemical Distribution of Heat Shock Protein 47 (HSP47) in Scirrhous Carcinoma of the Stomach," *Anticancer Research* 26( IA):71-78, 2006.

Lewis, M. P. et al., "Differential Response of Activated versus Non-activated Renal Fibroblasts to Tubular Epithelial Cells: A model of Initiation and Progression of Fibrosis?" *Experimental Nephrology* (1998) 6(2):132-143.

Pan, X. Q. et al., : "Strategy for the treatment of 1,3,6-8, acute myelogenous leukemia based on folate 11,12 receptor b -targeted liposomal doxorubicin combined with receptor induction using all-trans retinoic acid" *Blood* (2002) 100(2) :594-602.

Sauk, J, J. et al., "HSP47 A Novel Collagen Binding Serpin Chaperone, Autoantigen and Therapeutic Target." *Frontiers in Bioscience* (2005) 10:107-118.

Schurch, W et al., "Intermediate Filament Proteins and Actin Isoforms as Markers for Soft-tissue Tumor Differentiation and Origin. III. Hemangiopericytomas and Glomus Tumors," *American Journal of Pathology* (1990) 136(4.):771-786.

Shattuck-Brandt, R. L. et al., "Cyclooxygenase 2 Expression Is Increased in the Stroma of Colon Carcinomas from IL-I0$^{-/-}$ Mice" *Gastroenterology* (2000) 118(2):337-345.

Spanakis, E et al., "Discrimination of fibroblast subtypes by multivariate analysis of gene expression." *Int. J. Cancer* (1997) 71(3):402-409.

Svegliati-Baroni, G. et al., "Regulation of ERK/JNK/p70$^{S6K}$ in two rat models of liver injury and fibrosis" *Journal of Hepatology* 39(4) : 528-537, 2003.

Tsutani, H. et al., "Pharmacological studies of retinol palmitate and its clinical effect in patients with acute non-lymphocytic leukemia" *Leukemia Research* (1991) 15(6):463-471.

Watanabe, K et al., "n-Caldesmon as a Specific Marker for Smooth Muscle Tumors" *Am. J. Clin. Pathol.* (2000) 113(1):663-668.

Extended Search Report issued on Sep. 17, 2013 in European Application Nio. 08739842, filed on Mar. 28, 2008.

Office Action dated Jun. 20, 2013 for Chinese Patent Application no. 200880010916.8, filed on Aug. 8, 2009.

Elias et al., "Retinoids, cancer and the skin" International Journal of Skin Venereology, (1982) 3:156-159.

Elias et al., "Retinoids, cancer and the skin" Arch Dermatol (1981) 117:160-180.

Office Action dated Jan. 28, 2014 for Chinese Application No. 200880010916.8, filed Mar. 28, 2008.

Office Action dated Jan. 30, 2014 in Canadian Application No. 2,682,493, filed Mar. 28, 2008.

\* cited by examiner

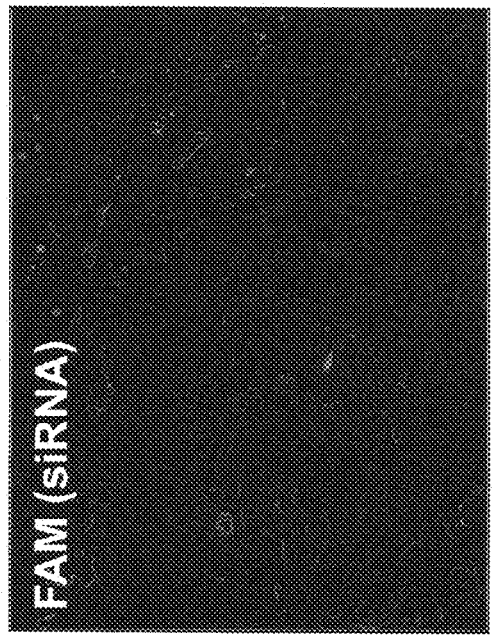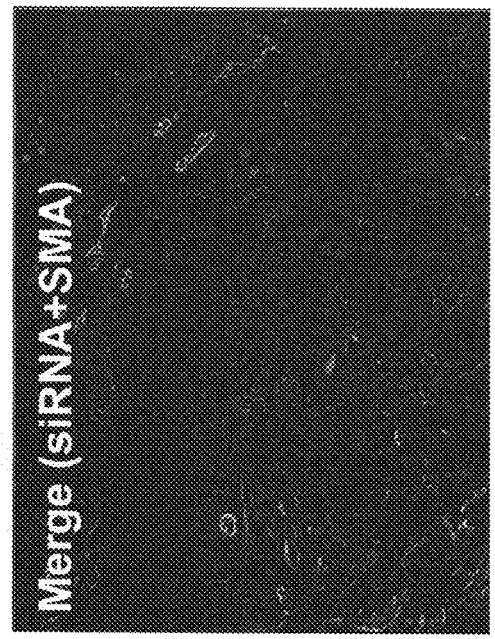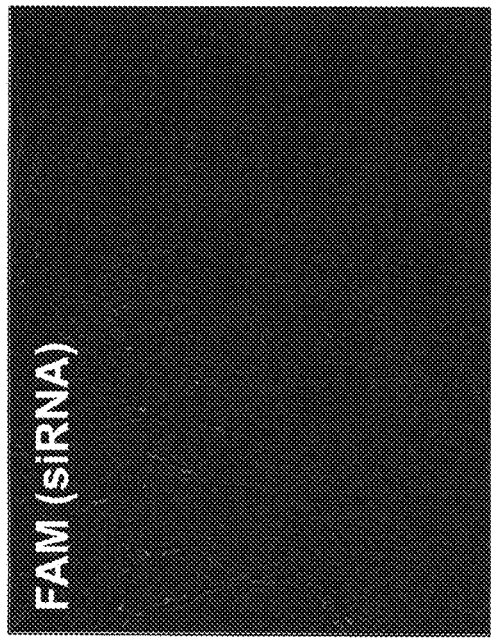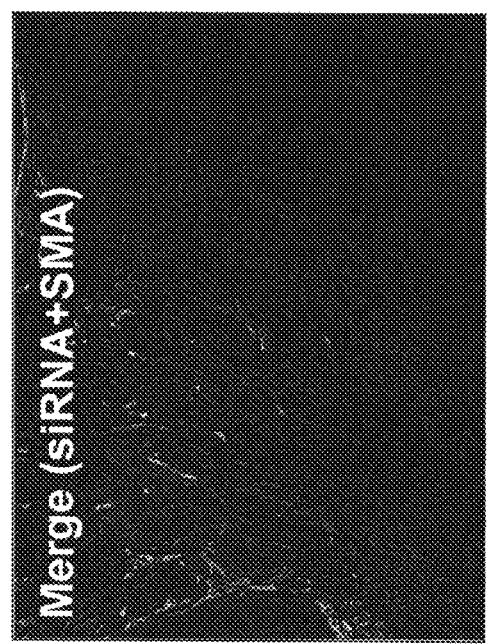
Fig. 21

SEQUENCE LISTING

```
<160> NUMBER OF SEQ ID NOS: 8

<210> SEQ ID NO 1
<211> LENGTH: 27
<212> TYPE: RNA
<213> ORGANISM: Artificial Sequence
<220> FEATURE:
<223> OTHER INFORMATION: Sense strand of gp46siRNAseqA

<400> SEQUENCE: 1
guuccaccau aagaugguag acaacag                                        27

<210> SEQ ID NO 2
<211> LENGTH: 27
<212> TYPE: RNA
<213> ORGANISM: Artificial Sequence
<220> FEATURE:
<223> OTHER INFORMATION: Antisense strand of gp46siRNAseqA

<400> SEQUENCE: 2
guugucuacc aucuuauggu ggaacau                                        27

<210> SEQ ID NO 3
<211> LENGTH: 27
<212> TYPE: RNA
<213> ORGANISM: Artificial Sequence
<220> FEATURE:
<223> OTHER INFORMATION: Sense strand of gp46siRNAseqB

<400> SEQUENCE: 3
ccacaaguuu uauauccaau cuagcag                                        27

<210> SEQ ID NO 4
<211> LENGTH: 27
<212> TYPE: RNA
<213> ORGANISM: Artificial Sequence
```

```
-continued

<220> FEATURE:
<223> OTHER INFORMATION: Antisense strand of gp46siRNAseqB

<400> SEQUENCE: 4
gcuagauugg auauaaaacu uguggau                                         27

<210> SEQ ID NO 5
<211> LENGTH: 27
<212> TYPE: RNA
<213> ORGANISM: Artificial Sequence
<220> FEATURE:
<223> OTHER INFORMATION: Sense strand of gp46siRNAseqC

<400> SEQUENCE: 5
cuagagccau uacauuacau ugacaag                                         27

<210> SEQ ID NO 6
<211> LENGTH: 27
<212> TYPE: RNA
<213> ORGANISM: Artificial Sequence
<220> FEATURE:
<223> OTHER INFORMATION: Antisense strand of gp46siRNAseqC

<400> SEQUENCE: 6
ugucaaugua auguaauggc ucuagau                                         27

<210> SEQ ID NO 7
<211> LENGTH: 27
<212> TYPE: RNA
<213> ORGANISM: Artificial Sequence
<220> FEATURE:
<223> OTHER INFORMATION: Sense strand of random siRNA

<400> SEQUENCE: 7
cgauucgcua gaccggcuuc auugcag                                         27

<210> SEQ ID NO 8
<211> LENGTH: 27
<212> TYPE: RNA
<213> ORGANISM: Artificial Sequence
<220> FEATURE:
<223> OTHER INFORMATION: Antisense strand of random siRNA

<400> SEQUENCE: 8
gcaaugaagc cggucuagcg aaucgau                                         27
```

US 8,686,052 B2

TARGETING AGENT FOR CANCER CELL OR CANCER-ASSOCIATED FIBROBLAST

TECHNICAL FIELD

The present invention relates to a targeting agent to a cell selected from the group consisting of a cancer cell and a cancer-associated fibroblast (CAF: cancer-associated fibroblast or carcinoma-associated fibroblast), a substance delivery carrier to the cell, the carrier containing the targeting agent, and an anticancer composition, an anti-CAF composition, and a method for treating a cancer utilizing same.

BACKGROUND ART

Cancer is one of the most significant diseases confronting mankind, and much research effort is going into the treatment thereof. In cancer treatment, particularly in the medical therapy of cancer, various anticancer agents for suppressing the growth of cancer cells have been developed, and some degree of success has been achieved, but since such drugs suppress the growth of not only cancer cells but also normal cells, there are problems with various side effects such as nausea and vomiting, hair loss, myelosuppression, kidney damage, and nerve damage. As an approach to reduce such side effects, attempts have been made in recent years to specifically deliver an anticancer agent to cancer cells or cancer tissue. By specific delivery of an anticancer agent, is it is not only possible to prevent the anticancer agent from reaching normal cells and reduce the side effects, but also to obtain the economic benefit that the dose of the anticancer agent can be decreased.

As a concrete example of a delivery method, there have been developed techniques such as passive targeting in which the EPR (enhanced permeability and retention) effect is utilized and active targeting in which a drug is modified by a ligand for a surface molecule that is specifically expressed on cancer cells. As molecules that can be utilized in active targeting, molecules that are endocytosed into cells as a result of ligand bonding, such as, for example, CD19, HER2, a transferrin receptor, a folate receptor, a VIP receptor, EGFR (Nonpatent Publication 1), RAAG10 (Patent Publication 1), PIPA (Patent Publication 2), and KID3 (Patent Publication 3) have been reported. However, none of the delivery methods are yet satisfactory, and there has been a further desire for the development of cancer cell-specific delivery methods.

Furthermore, in the medical therapy of cancer, from the idea that a cancer can be cured by killing the cancer cells themselves, various anticancer agents targeted at cancer cells have been developed and used. However, such attempts could not always achieve satisfactory results because of the above-mentioned problems with side effects, or the occurrence of additional phenomena such as relapse due to minimal residual disease, resistance of tumor cells to the anticancer agent, etc.

On the other hand, as a result of recent research, it has gradually become clear that the environment around a cancer, for example, interstitial tissue which includes blood vessels, ECM, and fibroblasts, plays an important role in the onset and progression of the cancer. For example, Camps et al. (see Nonpatent Publication 2) reported that when an athymic nude mouse was inoculated with tumor cells that do not form a tumor on their own or for which the tumor formation rate is low, together with tumorigenic fibroblasts, rapid and marked formation of a tumor was observed, and Olumi et al. (see Nonpatent Publication 3) reported that when peritumoral fibroblasts (i.e. CAFs) from a prostate tumor patient were grafted on an athymic animal together with human prostate cells, the neoplastic growth thereof was markedly accelerated. Furthermore, it has been clarified that a bioactive substance such as PDGF (platelet-derived growth factor), TGF-β (transforming growth factor-β), HGF (hepatocyte growth factor), or SDF-1 (stromal cell-derived factor-1) produced in the interstitium is involved in such growth of a tumor (see Nonpatent Publication 4).

From these findings, the importance of the environment around a cancer has been brought to the fore, and new treatment methods that, rather than the cancer cells themselves, are targeted at the environment around them have been investigated. Among them, CAFs, which secrete various bioactive substances and are deeply involved in the onset and progression of cancer, have been attracting attention in recent years, but fundamental research thereinto only has a short history of 10 or so years, and although some of the cancer treatment methods that are targeted at bioactive substances secreted from CAFs have been recognized as having some degree of effect, in the current situation none is recognized as having any effect as a cancer treatment method targeted at CAFs themselves (see Nonpatent Publication 4).

REFERENCE LIST

Patent Publication 1. JP 2005-532050 A
Patent Publication 2. JP 2006-506071 A
Patent Publication 3. JP 2007-529197 A
Patent Publication 4. WO 2006/068232
Nonpatent Publication 1. Torchilin, AAPS J. 2007; 9(2): E128-47
Nonpatent Publication 2. Camps et al., Proc Natl Acad Sci USA. 1990; 87(1): 75-9
Nonpatent Publication 3. Olumi et al., Cancer Res. 1999; 59(19): 5002-11
Nonpatent Publication 4. Micke et al., Expert Opin Ther Targets. 2005; 9(6): 1217-33

DISCLOSURE OF INVENTION

Problems to be Solved by the Invention

It is an object of the present invention to provide a carrier that can deliver a substance such as a drug specifically to a cancer cell, and a cancer drug and a cancer treatment method utilizing same, and also to provide a carrier that can deliver a drug specifically to a CAF, and a cancer drug and a cancer treatment method utilizing same.

Means for Solving the Problems

While searching for a novel cancer treatment method, the present inventors have found that there is not yet a carrier that can deliver a drug specifically to CAFs, and as a result of continuing an intensive investigation in order to develop such a carrier, it has been found that a carrier containing a retinoid as a targeting agent specifically accelerates drug delivery to CAFs. As a result of further investigation into the above carrier, it has been found that the carrier also specifically accelerates the delivery of a substance to cancer cells, and the present invention has thus been accomplished.

It is known that a carrier containing retinol delivers a drug to stellate cells storing retinol (see Patent Publication 4), but it was not known until now that it specifically accelerates the delivery of a drug to cancer cells or CAFs.

That is, the present invention relates to:

(1) a targeting agent to a cell selected from the group consisting of a cancer cell and a cancer-associated fibroblast, the targeting agent including a retinoid;

(2) the targeting agent of (1), wherein the retinoid includes retinol;

(3) a substance delivery carrier to a cell selected from the group consisting of a cancer cell and a cancer-associated fibroblast, the carrier including the targeting agent of (1) or (2);

(4) the carrier of (3), wherein the content of the targeting agent is 0.2 to 20 wt % of the entire carrier;

(5) the carrier of (3) or (4), wherein the molar ratio of the targeting agent to constituent components of the carrier other than the targeting agent is 8:1 to 1:4;

(6) an anticancer composition that includes the targeting agent of (1) or (2) or the carrier of any one of (3) to (5), and a drug that controls the activity or growth of a cancer cell and/or a cancer-associated fibroblast;

(7) an anti-cancer-associated fibroblast composition that includes the targeting agent of (1) or (2) or the carrier of any one of (3) to (5), and a drug that controls the activity or growth of a cancer-associated fibroblast;

(8) the composition of (6), wherein the drug that controls the activity or growth of a cancer cell is an anticancer agent;

(9) the composition of any one of (6) to (8), wherein the drug that controls the activity or growth of a cancer-associated fibroblast is selected from the group consisting of an inhibitor of activity or production of a bioactive substance selected from the group consisting of TGF-β, HGF, PDGF, VEGF (vascular endothelial growth factor), IGF (insulin-like growth factor), MMP (matrix metalloproteinase), FGF (fibroblast growth factor), uPA (urokinase-type plasminogen activator), cathepsin, and SDF-1, a cell activity suppressor, a growth inhibitor, an apoptosis inducer, and an siRNA, ribozyme, antisense nucleic acid, DNA/RNA chimeric polynucleotide, or vector expressing same that targets one or more molecules from among an extracellular matrix constituent molecule produced by cancer-associated fibroblasts and a molecule involved in the production or secretion of the extracellular matrix constituent molecule;

(10) the composition of (9), wherein the molecule involved in the production or secretion of the extracellular matrix constituent molecule is HSP47;

(11) the composition of any one of (6) to (10), wherein the drug and the targeting agent or the carrier are mixed at a place of medical treatment or in the vicinity thereof; and

(12) a preparation kit for the composition of any one of (6) to (11), the kit including one or more containers containing singly or in combination the drug, the targeting agent, and as necessary carrier constituent substances other than the targeting agent.

Effects of the Invention

The carrier of the present invention specifically targets a cancer cell and a CAF, and efficiently delivers to a cancer cell and/or a CAF a desired substance or body such as, for example, a drug that controls the activity or growth of a cancer cell or a CAF, thus enabling a desired effect such as, for example, suppression of the activity or growth of a cancer cell or a CAF thereby curing cancer, suppressing the advance thereof, and preventing the onset thereof, to be achieved with the highest efficiency and the minimum side effects.

Since the anticancer composition of the present invention is based on the completely novel approach of treating a cancer by acting on a CAF in addition to a cancer cell itself, efficacy can be expected on cancers for which a conventional treatment method could not give satisfactory results and, furthermore, a synergistic effect due to combined use with a conventional anticancer agent, angiogenesis inhibitor, etc. can be anticipated.

Furthermore, since the carrier of the present invention can specifically deliver a substance to a cancer cell and a CAF, it can be utilized for specifically labeling a cancer cell and a CAF, gene transfer, etc.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 21 is a photographic diagram showing the localization of siRNA in the tumor tissue of a tumor-bearing mouse to which VA-lip-siRNA or lip-siRNA had been intravenously administered. The right-hand side shows an individual to which VA-lip-siRNA had been administered, the left-hand side shows an individual to which lip-siRNA had been administered, the top shows an FAM image, and the bottom shows a merged FAM and Cy3 image. The magnification is 200 times.

BEST MODE FOR CARRYING OUT THE INVENTION

Figure 1:
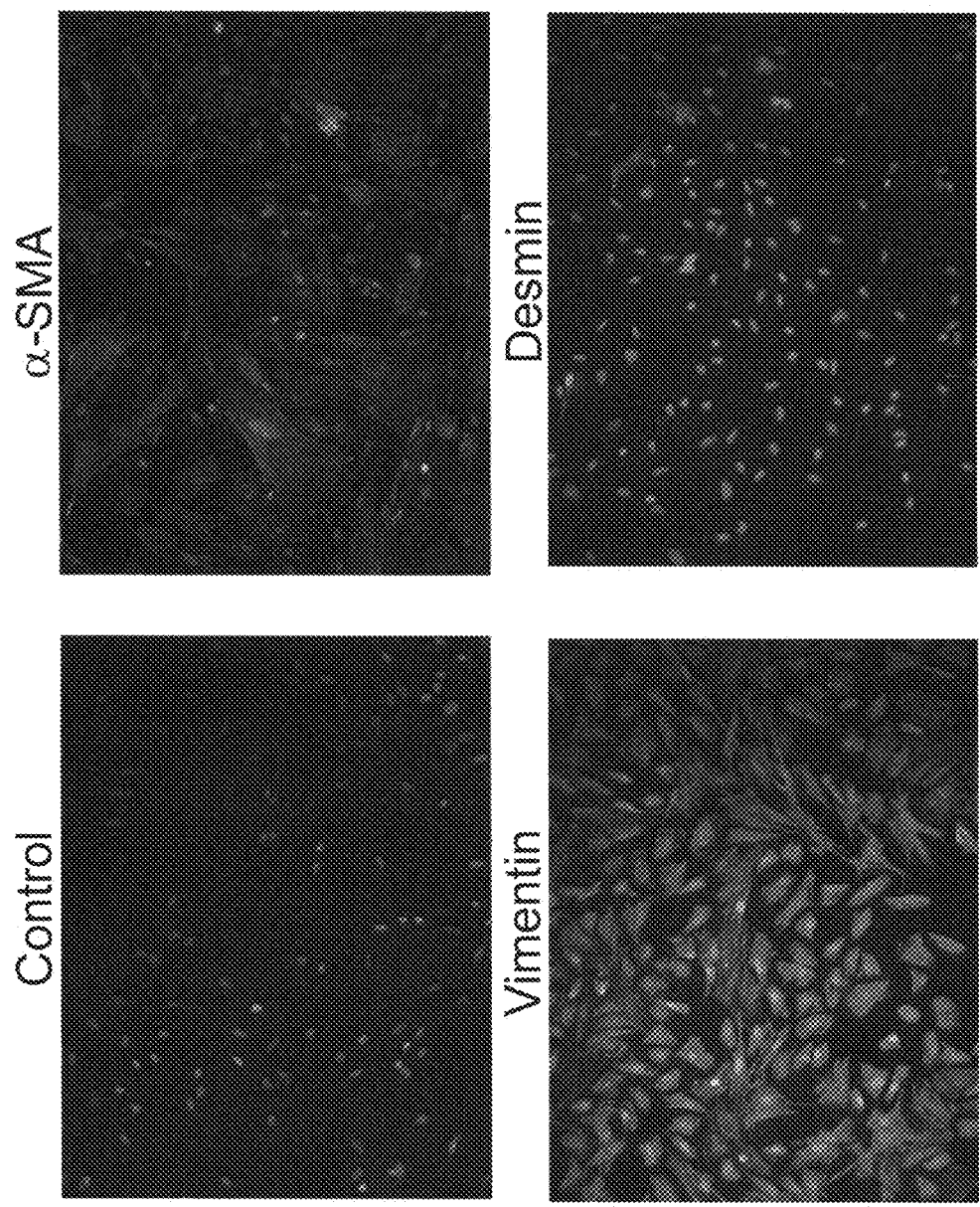
FIG. 1 is a photographic diagram of cancer tissue-derived cells immunostained with respect to α-SMA, vimentin, and desmin.

The present invention is explained in detail below.

In the present invention, the cancer cell is not particularly limited, and examples thereof include a cancer cell in sarcomas such as fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, and osteosarcoma, any kind of cancer such as brain tumor, head and neck carcinoma, breast carcinoma, lung carcinoma, esophageal carcinoma, stomach carcinoma, duodenal carcinoma, appendiceal carcinoma, colon carcinoma, rectal carcinoma, hepatic carcinoma, pancreatic carcinoma, gallbladder carcinoma, bile duct carcinoma, anal carcinoma, kidney carcinoma, ureteral carcinoma, bladder carcinoma, prostate carcinoma, penile carcinoma, testicular carcinoma, uterine carcinoma, ovarian carcinoma, vulvar carcinoma, vaginal carcinoma, and skin carcinoma and, furthermore, leukemia, malignant lymphoma, etc. In the present invention, 'cancer' includes carcinoma and sarcoma. The cancer cell in the present invention is therefore present at any site such as, for example, the brain, head and neck, breast, limbs, lung, heart, thymus, esophagus, stomach, small intestine (duodenum, jejunum, ileum), large intestine (colon, cecum, appendix, rectum), liver, pancreas, gallbladder, anus, kidney, ureter, bladder, prostate, penis, testis, uterus, ovary, vulva, vagina, skin, striated muscle, smooth muscle, synovial membrane, cartilage, bone, thyroid, adrenal gland, peritoneum, mesentery, bone marrow, blood, vascular system, lymphatic system such as lymph nodes, lymphatic fluid, etc.

In one embodiment of the present invention, a cancer cell is preferably present at sites other than the liver and pancreas. Therefore, in this embodiment, the cancer cell is preferably present in, for example, the brain, head and neck, breast, limbs, lung, heart, thymus, esophagus, stomach, small intestine (duodenum, jejunum, ileum), large intestine (colon, cecum, appendix, rectum), gallbladder, anus, kidney, ureter, bladder, prostate, penis, testis, uterus, ovary, vulva, vagina, skin, striated muscle, smooth muscle, synovial membrane, cartilage, bone, thyroid, adrenal gland, peritoneum, mesentery, bone marrow, blood, vascular system, lymphatic system such as lymph nodes, lymphatic fluid, etc. Furthermore, in one embodiment of the present invention, a cancer cell is preferably that other than a hepatic carcinoma cell and a pancreatic carcinoma cell.

In the present invention, a cancer-associated fibroblast (CAF) means an α-SMA (smooth muscle actin) positive fibroblast present in the interior and/or the periphery of a cancer lesion. The presence of a CAF is confirmed with respect to various cancers such as colon carcinoma, lung carcinoma, prostate carcinoma, breast carcinoma, stomach carcinoma, bile duct carcinoma, and basal cell carcinoma.

In the present invention, whether or not given cell is CAF is determined by the following method. That is, a cell present in the interior and/or the periphery of the cancer lesion is immunostained with a labeled antibody for α-SMA, which is a CAF marker, for example, FITC-labeled anti α-SMA antibody or Cy3-labeled anti α-SMA antibody, and that detected by α-SMA is determined to be a CAF.

Cancer accompanied by CAF in the present invention is not particularly limited, and examples thereof include solid carcinomas such as brain tumor, head and neck carcinoma, breast carcinoma, lung carcinoma, esophageal carcinoma, stomach carcinoma, duodenal carcinoma, appendiceal carcinoma, colon carcinoma, rectal carcinoma, hepatic carcinoma, pancreatic carcinoma, gallbladder carcinoma, bile duct carcinoma, anal carcinoma, kidney carcinoma, ureteral carcinoma, bladder carcinoma, prostate carcinoma, penile carcinoma, testicular carcinoma, uterine carcinoma, ovarian carcinoma, vulvar carcinoma, vaginal carcinoma, and skin carcinoma. Furthermore, a CAF typically accompanies a carcinoma, but as long as similar properties are possessed, it may accompany a malignant solid tumor other than a carcinoma, for example, a sarcoma such as fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, or osteosarcoma, and they are included in the scope of the present invention.

In one embodiment of the present invention, a CAF is preferably present at sites other than the liver and pancreas. Therefore, in this embodiment, the CAF is present in, for example, the brain, head and neck, breast, limbs, lung, heart, thymus, esophagus, stomach, small intestine (duodenum, jejunum, ileum), large intestine (colon, cecum, appendix, rectum), gallbladder, anus, kidney, ureter, bladder, prostate, penis, testis, uterus, ovary, vulva, vagina, skin, striated muscle, smooth muscle, synovial membrane, cartilage, bone, thyroid, adrenal gland, peritoneum, mesentery, etc.

A retinoid is a member of the class of compounds having a skeleton in which four isoprenoid units are bonded in a head-to-tail manner. See G. P. Moss, "Biochemical Nomenclature and Related Documents," 2nd Ed. Portland Press, pp. 247-251 (1992). Vitamin A is a generic descriptor for a retinoid qualitatively showing the biological activity of retinol. Retinoid in the present invention promotes specific substance delivery to a cancer cell and a CAF (that is, the substance is targeted at these cells). Such a retinoid is not particularly limited, and examples thereof include retinoid derivatives such as retinol, retinal, retinoic acid, an ester of retinol and a fatty acid, an ester of an aliphatic alcohol and retinoic acid, etretinate, tretinoin, isotretinoin, adapalene, acitretine, tazarotene, and retinol palmitate, and vitamin A analogues such as fenretinide (4-HPR), and bexarotene.

In the present invention, retinoid has the same meaning as retinoid derivative and/or vitamin A analogue. Although the mechanism by which a retinoid promotes specific substance delivery to a cancer cell and a CAF has not been completely elucidated, it is surmised that uptake via a certain type of receptor on the surface of a cancer cell and a CAF is involved.

Among them, retinol, retinal, retinoic acid, an ester of retinol and a fatty acid (e.g. retinyl acetate, retinyl palmitate, retinyl stearate, and retinyl laurate) and an ester of an aliphatic alcohol and retinoic acid (e.g. ethyl retinoate) are preferable from the viewpoint of efficiency of specific delivery of a substance to a cancer cell and a CAF.

All retinoid isomers, such as cis-trans, are included in the scope of the present invention. The retinoid may be substituted with one or more substituents. The retinoid in the present invention includes a retinoid in an isolated state as well as in a solution or mixture state with a medium that can dissolve or retain the retinoid.

One aspect of the present invention relates to a targeting agent comprising a retinoid, to a cell selected from the group consisting of a cancer cell and a cancer-associated fibroblast. The targeting referred to here means enabling a substance such as a drug or a drug carrier to be delivered to a specific target such as a specific cell or tissue (in the present invention a cell selected from the group consisting of a cancer cell and a cancer-associated fibroblasts) more rapidly, efficiently, and/or in a larger quantity than with non-target cell or tissue and a substance that is non-targeted, that is, it enables specific delivery to a target, and the targeting agent means a substance that can subject a substance to the above-mentioned targeting when it binds to or reacts with the substance. Therefore, in the present specification, for example, 'cancer cell-specific carrier or composition' has the same meaning as 'cancer cell-targeted carrier or composition'. When the targeting agent is in the configuration of a molecule, this has the same meaning as a targeting molecule.

The targeting agent of the present invention may be formed from the above-mentioned retinoid on its own or may include a constituent element other than the retinoid, for example, an element for promoting or stabilizing binding between a targeting agent and a carrier or a drug, an element for protecting the retinoid during storage, during use in a production of a formulation, or during storage of a formulation, or a spacer for spatially separating the retinoid from a carrier or a drug. The targeting agent of the present invention is bound to any carrier or drug, and can target this carrier or drug at a cell selected from the group consisting of a cancer cell and a cancer-associated fibroblast.

Furthermore, the present invention relates to a substance delivery carrier to a cell selected from the group consisting of a cancer cell and a cancer-associated fibroblast, the carrier including the targeting agent. The carrier of the present invention may be formed from the targeting agent on its own or may be formed by making the targeting agent bind to or be enclosed in another constituent component, other than the targeting agent, of the carrier. Therefore, the carrier of the present invention may include a constituent component other than the targeting agent. Such a component is not particularly limited, and any component known in the medicinal and pharmaceutical fields may be used, but those that can enclose the targeting agent, and the retinoid in particular, or can bind thereto are preferable.

Examples of such a component include a lipid, for example, a phospholipid such as glycerophospholipid, a sphingolipid such as sphingomyelin, a sterol such as cholesterol, a vegetable oil such as soybean oil or poppy seed oil, a mineral oil, and a lecithin such as egg-yolk lecithin, but the examples are not limited thereto. Among them, those that can form a liposome are preferable, for example, a natural phospholipid such as lecithin, a semisynthetic phospholipid such as dimyristoylphosphatidylcholine (DMPC), dipalmitoylphosphatidylcholine (DPPC), or distearoylphosphatidylcholine (DSPC), dioleylphosphatidylethanolamine (DOPE), dilauroylphosphatidylcholin (DLPC), and cholesterol.

A particularly preferred component is a component that can avoid capture by the reticuloendothelial system, and examples thereof include cationic lipids such as N-($\alpha$-trimethylammonioacetyl)-didodecyl-D-glutamate chloride (TMAG), N,N',N'',N'''-tetramethyl-N,N',N'',N'''-tetrapalmitylspermine (TMTPS), 2,3-dioleyloxy-N-[2(sperminecarboxamido)ethyl]-N,N-dimethyl-1-propanaminium trifluoroacetate (DOSPA), N-[1-(2,3-dioleyloxy)propyl]-N,N,N-trimethylammonium chloride (DOTMA), dioctadecyldimethylammonium chloride (DODAC), didodecylammonium bromide (DDAB), 1,2-dioleyloxy-3-trimethylammoniopropane (DOTAP), 3$\beta$[N—(N',N'-dimethylaminoethane)caramoyl]cholesterol (DC-Chol), 1,2-dimyristoyloxypropyl-3-dimethylhydroxyethylammonium (DMRIE), and O,O'-ditetradecanoyl-N-($\alpha$-trimethylammonioacetyl)diethanolamine chloride (DC-6-14).

The binding of the targeting agent to the carrier of the present invention or the enclosing of it therein is also possible by binding or enclosing the targeting agent to or in a constituent component, other than the targeting agent, of the carrier by a chemical and/or physical method. Alternatively, the binding or enclosing the targeting agent to or in the carrier of the present invention can also be carried out by mixing the targeting agent and a constituent component, other than the targeting agent, of the carrier when preparing the carrier. The amount of targeting agent bound to or enclosed in the carrier of the present invention may be, as a weight ratio in the carrier constituent components including the targeting agent, 0.01% to 100%, preferably 0.2% to 20%, and more preferably 1% to 5%. The binding or enclosing of the targeting agent to or in the carrier may be carried out before a drug, etc. is supported on the carrier, may be carried out at the same time as mixing the carrier, the targeting agent, and a drug, etc., or may be carried out by mixing the targeting agent with a carrier on which a drug, etc. is already supported. Therefore, the present invention also relates to a process for producing a formulation targeted at a cell selected from the group consisting of a cancer cell and a CAF, the process including a step of binding a targeting agent to any existing drug binding carrier or drug encapsulating carrier, for example, a liposomal formulation such as DaunoXome®, Doxil, Caelyx®, or Myocet®.

The configuration of the carrier of the present invention may be any configuration as long as a desired substance or body can be carried to a target cancer cell or CAF, and although not limited thereto, examples thereof include a macromolecular micelle, a liposome, an emulsion, microspheres, and nanospheres. The size of the carrier of the present invention can be changed according to the type, etc. of drug. Such a size is not particularly limited and, for example, the diameter is preferably 50 to 200 μm, and more preferably 75 to 150 μm. This is because such a size is suitable for exhibiting the EPR effect which promotes the accumulation in cancer tissue, and is also suitable for delivery of a drug that controls the activity or growth of a cancer cell and/or a CAF, which is described later. Such a diameter is measured by a dynamic light scattering method.

In the carrier of the present invention, the molar ratio (abundance ratio) of the targeting agent to constituent components, other than the targeting agent, of the carrier when administered is preferably 8:1 to 1:4, more preferably 4:1 to 1:2, yet more preferably 3:1 to 1:1, and particularly preferably 2:1. Without being bound by theory, it is believed that such a molar ratio is effective in giving good binding or enclosing of the targeting agent to or in a carrier (that is, the targeting function of the targeting agent is not impaired) and in specifically delivering a substance to a cancer cell or a CAF.

In the present invention, from the viewpoint of high delivery efficiency, wide selection of substances to be delivered, ease of making a formulation, etc., a liposomal configuration is preferable among the configurations, and a cationic liposome that includes a cationic lipid is particularly preferable.

The carrier of the present invention may contain a substance to be carried within its interior, may be attached to the exterior of a substance to be carried, or may be mixed with a substance to be carried, as long as the targeting agent contained therein is present in such a configuration that it can exhibit a targeting function. The 'exhibiting a targeting function' referred to here means that the carrier containing the targeting agent reaches and/or is taken up by the target cancer cell and/or CAF more rapidly, efficiently and/or in a larger quantity than with a carrier not containing the targeting agent, and this may easily be confirmed by, for example, adding a labeled or label-containing carrier to cultured cancer cell and/or CAF, and analyzing sites where the label is present after a predetermined period of time. Unpredictably, the present inventors have found that specific substance delivery to a cancer cell and/or a CAF is efficiently realized by at least partially exposing the targeting agent on the exterior of a formulation containing the carrier at the latest by the time it reaches the cancer cell and/or CAF. The present inventors consider this to be a phenomenon in which the targeting agent exposed on the exterior of the formulation containing the carrier is taken up by the cancer cell and/or CAF more efficiently than by normal diffusion, via a certain type of receptor on the surface of the cancer cell and/or CAF. A technique for exposing the targeting agent on the exterior of the formulation containing the carrier is not particularly limited; for example, when preparing a carrier, excess targeting agent may be added relative to constituent components, other than the targeting agent, of the carrier. More specifically, in order to efficiently expose the targeting agent on the exterior of a formulation containing the carrier, the molar ratio (compounding ratio) of the targeting agent to constituent components, other than the targeting agent, of the carrier when compounded is preferably 8:1 to 1:4, more preferably 4:1 to 1:2, yet more preferably 3:1 to 1:1, and particularly preferably 2:1.

The substance or body that is delivered by the present carrier is not particularly limited, and it preferably has a size such that it can physically move within the body of a living being from an administration site to a lesion site where a cancer cell and/or a CAF is/are present. Therefore, the carrier of the present invention can carry not only a substance such as an atom, a molecule, a compound, a protein, or a nucleic acid, but also a body such as a vector, a virus particle, a cell, a drug-releasing system formed from one or more elements, or a micromachine. The above substance or body preferably has the property of having some influence on a cancer cell and/or a CAF, and examples thereof include those that label a cancer cell and/or a CAF and those that control (e.g. increase or suppress) the activity and growth of a cancer cell and/or a CAF.

Therefore, in one embodiment of the present invention, the substance that the carrier delivers is 'a drug controlling the activity or growth of a cancer cell and/or a CAF'. The activity of a cancer cell referred to here indicates various activities such as secretion, uptake, migration, etc. exhibited by a cancer cell, and in the present invention among them it typically means, in particular, activities involved in the onset, progression, recurrence and/or metastasis of a cancer, and the manifestation, exacerbation, etc. of symptoms such as cachexia. Examples of such activities include, but are not limited to, the production/secretion of parathyroid hormone-related protein (PTHrP), immunosuppressive acidic protein (IAP), etc.

Furthermore, the activity of a CAF means various activities such as secretion, uptake, migration, etc. exhibited by CAF, and in the present invention it typically means activities involved in the onset and/or progression of a cancer in particular. Examples of such activities include the production/secretion of bioactive substances such as TGF-β, HGF, PDGF, VEGF, IGF (IFG1, IGF2, etc.), MMP (MMP1, 2, 3, 9, 11, 13, 14, etc.), FGF (FGF7, bFGF, etc.), uPA, cathepsin, and SDF-1, and extracellular matrix components such as collagen, proteoglycan, tenascin, fibronectin, thrombospondin, osteopontin, osteonectin, and elastin.

Therefore, the drug controlling the activity and growth of a cancer cell may be any drug that directly or indirectly suppresses the physical, chemical, and/or physiological actions, etc. of a cancer cell related to the onset, progression, and/or recurrence of a cancer, and while not being limited thereto, it includes anticancer agents that suppress the onset, progression, and/or recurrence of a cancer, and examples thereof include, but are not limited to, alkylating agents such as ifosfamide, nimustine hydrochloride, cyclophosphamide, dacarbazine, melphalan, and ranimustine, antimetabolites such as gemcitabine hydrochloride, enocitabine, cytarabine ocfosfate, a cytarabine formulation, tegafur/uracil, a tegafur/gimeracil/oteracil potassium mixture, doxifluridine, hydroxycarbamide, fluorouracil, methotrexate, and mercaptopurine, antitumor antibiotics such as idarubicin hydrochloride, epirubicin hydrochloride, daunorubicin hydrochloride, daunorubicin citrate, doxorubicin hydrochloride, pirarubicin hydrochloride, bleomycin hydrochloride, peplomycin sulfate, mitoxantrone hydrochloride, and mitomycin C, alkaloids such as etoposide, irinotecan hydrochloride, vinorelbine tartrate, docetaxel hydrate, paclitaxel, vincristine sulfate, vindesine sulfate, and vinblastine sulfate, hormone therapy agents such as anastrozole, tamoxifen citrate, toremifene citrate, bicalutamide, flutamide, and estramustine phosphate, platinum complexes such as carboplatin, cisplatin, and nedaplatin, angiogenesis inhibitors such as thalidomide, neovastat, and bevacizumab, L-asparaginase etc., drugs inhibiting the activity or production of the above bioactive substances, such as, for example, antibodies and antibody fragments that neutralize the above bioactive substances, and substances that suppress expression of the above bioactive substances, such as an siRNA, a ribozyme, an antisense nucleic acid (including RNA, DNA, PNA, and a composite thereof), substances that have a dominant negative effect such as a dominant negative mutant, vectors expressing same, cell activity inhibitors such as a sodium channel inhibitor, cell-growth inhibitors, and apoptosis inducers such as compound 861 and gliotoxin. Furthermore, the 'drug controlling the activity or growth of a cancer cell' in the present invention may be any drug that directly or indirectly promotes the physical, chemical, and/or physiological actions, etc. of a cancer cell directly or indirectly related to suppressing the onset, progression, and/or recurrence of a cancer. Among the above-mentioned drugs, an anticancer agent is particularly preferable from the viewpoint of therapeutic effect, etc.

Moreover, the 'drug controlling the activity or growth of a CAF' referred to here may be any drug that directly or indirectly suppresses the physical, chemical, and/or physiological actions, etc. of a CAF related to the onset and/or progression of a cancer, and examples thereof include, without being limited thereto, drugs that inhibit the activity or production of the above bioactive substances, for example, TGF-β II receptors that antagonize TGF-β (truncated TGF-β II receptor, soluble TGF-β II receptor, etc.), MMP inhibitors such as batimastat, antibodies and antibody fragments that neutralize the above bioactive substances, substances that suppress the expression of the above bioactive substances, such as an siRNA, a ribozyme, an antisense nucleic acid (including RNA, DNA, PNA, and composites thereof), substances that have a dominant negative effect such as a dominant negative mutant, vectors expressing same, cell activation inhibitors such as a sodium channel inhibitor, cell-growth inhibitors such as alkylating agents (e.g. ifosfamide, nimustine hydrochloride, cyclophosphamide, dacarbazine, melphalan, ranimustine, etc.), antitumor antibiotics (e.g. idarubicin hydrochloride, epirubicin hydrochloride, daunorubicin hydrochloride, daunorubicin citrate, doxorubicin hydrochloride, pirarubicin hydrochloride, bleomycin hydrochloride, peplomycin sulfate, mitoxantrone hydrochloride, mitomycin C, etc.), antimetabolites (e.g. gemcitabine hydrochloride, enocitabine, cytarabine ocfosfate, a cytarabine formulation, tegafur/uracil, a tegafur/gimeracil/oteracil potassium mixture, hydroxycarbamide, fluorouracil, methotrexate, and mercaptopurine, etc.), alkaloids such as etoposide, irinotecan hydrochloride, vinorelbine tartrate, docetaxel hydrate, paclitaxel, vincristine sulfate, vindesine sulfate, and vinblastine sulfate, and platinum complexes such as carboplatin, cisplatin, nedaplatin, etc., and apoptosis inducers such as compound 861 and gliotoxin. Furthermore, the 'drug controlling the activity or growth of a CAF' referred to in the present invention may be any drug that directly or indirectly promotes the physical, chemical, and/or physiological actions, etc. of a CAF directly or indirectly related to suppressing the onset and/or progression of a cancer.

Other examples of the 'drug controlling the activity or growth of a CAF' include drugs controlling the metabolism of an extracellular matrix, for example, collagen, and examples thereof include substances having an effect in suppressing the expression of a target molecule, such as an siRNA, a ribozyme, and an antisense nucleic acid (including RNA, DNA, PNA, or a composite thereof), which are targeted at an extracellular matrix constituent molecule produced by a CAF or targeted at one or more molecules involved in the production or secretion of the extracellular matrix constituent molecule, substances having a dominant negative effect such as a dominant negative mutant, and vectors expressing same.

An siRNA is a double strand RNA having a sequence specific to a target molecule such as an mRNA, and suppresses the expression of a substance, for example, a protein, formed by the target molecule, by promoting the decomposition of the target molecule (RNA interference). Since Fire et al. published the principle (Nature, 391: 806-811, 1998), a wide range of research has been carried out into the optimization of siRNAs, and a person skilled in the art is familiar with such techniques. Furthermore, intensive research has been carried out into substances, other than siRNAs, that cause RNA interference or a gene expression inhibition reaction, and at present there are a large number of such substances.

For example, JP 2003-219893 A discloses a double strand polynucleotide formed from DNA and RNA that inhibits the expression of a target gene. This polynucleotide may be either a DNA/RNA hybrid in which one of the double strands is DNA and the other is RNA, or a DNA/RNA chimera in which a portion of the same strand is DNA and the other portion is RNA. Such a polynucleotide is preferably formed from 19 to 25 nucleotides, more preferably 19 to 23 nucleotides, and yet more preferably 19 to 21 nucleotides; in the case of a DNA/RNA hybrid it is preferable that the sense strand is DNA and the antisense strand is RNA, and in the case of a DNA/RNA chimera it is preferable that portion on the upstream side of the double strand polynucleotide is RNA. Such a polynucleotide may be prepared so as to have any sequence by a standard procedure of a known chemical synthetic method.

The target molecule is preferably a molecule that can completely suppress the production and/or secretion of an extracellular matrix constituent molecule, for example, and examples thereof include, without being limited thereto, HSP47. The gene sequence of HSP47 or a homologue thereof is disclosed as, for example, GenBank accession No. AB010273 (human), X60676 (mouse), and M69246 (rat, gp46).

Therefore, as the drug controlling the activity or growth of a CAF of the present invention, for example, an siRNA, a DNA/RNA hybrid, a chimeric polynucleotide, an antisense nucleic acid, etc, that are targeted at HSP47 are preferable.

The substance or body delivered by the carrier of the present invention may or may not be labeled. Labeling enables the success or failure of transport, increases and decreases in cancer cells or CAFs, etc. to be monitored, and is particularly useful at the testing/research level. A label may be selected from any label known to a person skilled in the art such as, for example, any radioisotope, magnetic material, a substance that binds to a labeling substance (e.g. an antibody), a fluorescent substance, a fluorophore, a chemiluminescent substance, an enzyme, etc.

In the present invention, 'to a cancer cell' or 'to a cancer-associated fibroblast' means that it is suitable to use cancer cells or cancer-associated fibroblasts as a target, and this includes it being possible to deliver a substance to a target cell, that is, a cancer cell or a cancer-associated fibroblast, more rapidly, efficiently, and/or in a larger quantity than to other cells (non-target cells), for example, a noncancer cell or a normal fibroblast. For example, the carrier of the present invention can deliver a substance to a cancer cell or a cancer-associated fibroblast at a rate and/or efficiency of at least 1.1 times, at least 1.2 times, at least 1.3 times, at least 1.5 times, at least 2 times, or even at least 3 times compared with other cells. The 'efficiency' referred to here means the proportion of cells to which a substance is delivered relative to all the cells of the evaluation target.

The present invention also relates to a composition that includes the targeting agent or carrier, and one or more types of the above-mentioned drugs controlling the activity or growth of a cancer cell and/or a CAF, the composition being for controlling the activity or growth of a cancer cell or for treating a cancer (anticancer composition), for controlling the activity or growth of a CAF (anti-CAF composition), or for treating a cancer in which CAF is involved, and use of the targeting agent or carrier in the production of these compositions.

In the present invention, the cancer is any malignant tumor, and examples thereof include fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, osteosarcoma and, furthermore, brain tumor, head and neck carcinoma, breast carcinoma, lung carcinoma, esophageal carcinoma, stomach carcinoma, duodenal carcinoma, appendiceal carcinoma, colon carcinoma, rectal carcinoma, hepatic carcinoma, pancreatic carcinoma, gallbladder carcinoma, bile duct carcinoma, anal carcinoma, kidney carcinoma, ureteral carcinoma, bladder carcinoma, prostate carcinoma, penile carcinoma, testicular carcinoma, uterine carcinoma, ovarian carcinoma, vulvar carcinoma, vaginal carcinoma, skin carcinoma, leukemia, and malignant lymphoma. The cancer may be or may not be accompanied by a CAF. In one embodiment of the present invention, the cancer is preferably a cancer other than hepatic carcinoma or pancreatic carcinoma. In another embodiment, the treatment of a cancer is preferably other than the prevention of hepatic carcinoma or pancreatic carcinoma.

Furthermore, the cancer in which CAF is involved in the present invention is not only a 'CAF-accompanied cancer' for which CAF is present in the interior or the periphery of the cancer, but also includes a cancer from which CAF is spatially separated but whose growth and activity are promoted by the above-mentioned bioactive substances released from CAF. Therefore, the cancer in which CAF is involved broadly means a malignant tumor, and includes any carcinoma, which is an epithelial malignant tumor, such as for example brain tumor, head and neck carcinoma, breast carcinoma, lung carcinoma, esophageal carcinoma, stomach carcinoma, duodenal carcinoma, appendiceal carcinoma, colon carcinoma, rectal carcinoma, hepatic carcinoma, pancreatic carcinoma, gallbladder carcinoma, bile duct carcinoma, anal carcinoma, kidney carcinoma, ureteral carcinoma, bladder carcinoma, prostate carcinoma, penile carcinoma, testicular carcinoma, uterine carcinoma, ovarian carcinoma, vulvar carcinoma, vaginal carcinoma, and skin carcinoma and, furthermore, any other malignant solid tumor, which is a nonepithelial malignant tumor, such as for example fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, and osteosarcoma. In the present invention, a cancer in which CAF is involved, selected from colorectal carcinoma, lung carcinoma, breast carcinoma, prostate carcinoma, stomach carcinoma, bile duct carcinoma, and a skin carcinoma such as basal cell carcinoma, can advantageously be treated due to a high degree of contribution of CAF to the growth. In one embodiment of the present invention, the cancer in which CAF is involved does not include hepatic carcinoma or pancreatic carcinoma. Furthermore, in another embodiment, the treatment of a cancer in which CAF is involved does not include the prevention of hepatic carcinoma or pancreatic carcinoma.

One embodiment of the anticancer composition of the present invention includes the targeting agent or the carrier, and a drug controlling the activity and growth of a cancer cell, and delivering this directly to a cancer cell allows an anticancer action to be exhibited. Another embodiment of the anticancer composition of the present invention includes the targeting agent or the carrier, and a drug controlling the activity or growth of a CAF, and delivering this to a CAF and controlling the activity or growth thereof allows an anticancer action to be exhibited indirectly. Yet another embodiment of the anticancer composition of the present invention includes the targeting agent or the carrier, and either one of a drug controlling the activity or growth of a cancer cell and a drug controlling the activity or growth of a CAF, or both thereof, and since the drug controlling the activity or growth of a cancer cell acts on a cancer cell, and the drug controlling the activity or growth of a CAF acts on a CAF, the anticancer action is doubled. In this embodiment, the drug controlling the activity or growth of a cancer cell and the drug controlling the activity or growth of a CAF may be identical to each other or different from each other.

In the composition of the present invention, as long as the targeting agent is present in a mode that allows a targeting function to be exhibited, the carrier may contain a substance to be carried within its interior, may be attached to the exterior of a substance to be carried, or may be mixed with a substance to be carried. Therefore, depending on the administration route, the manner in which the drug is released, etc., the composition may be covered with an appropriate material such as, for example, an enteric coating or a material that disintegrates over time, or may be incorporated into an appropriate drug release system.

The composition of the present invention may be administered via various routes including both oral and parenteral, and examples thereof include, but are not limited to, oral, intravenous, intramuscular, subcutaneous, local, rectal, intraarterial, intraportal, intraventricular, transmucosal, percutaneous, intranasal, intraperitoneal, intratumoral, intrapulmonary, and intrauterine routes, and it may be formulated into a dosage form suitable for each administration route. Such a dosage form and formulation method may be selected as appropriate from any known forms and methods (see e.g. Hyojun Yakuzaigaku (Standard Pharmaceutics), Ed. by Yoshiteru Watanabe et al., Nankodo, 2003).

Examples of dosage forms suitable for oral administration include, but are not limited to, powder, granules, tablet, capsule, liquid, suspension, emulsion, gel, and syrup, and examples of the dosage form suitable for parenteral administration include injections such as an injectable solution, an injectable suspension, an injectable emulsion, and an injection in a form that is prepared at the time of use. Formulations for parenteral administration may be a configuration such as an aqueous or nonaqueous isotonic aseptic solution or suspension.

The targeting agent, the carrier, or the composition of the present invention may be supplied in any configuration, but from the viewpoint of storage stability, it is preferably provided in a configuration that can be prepared at the time of use, for example in a configuration that allows a doctor and/or a pharmacist, a nurse, another paramedic, etc. to prepare it at the place of treatment or in the vicinity thereof. In this case, the targeting agent, the carrier, or the composition of the present invention is provided as one or more containers containing at least one essential constituent element therefor, and it is prepared prior to use, for example, within 24 hours prior to use, preferably within 3 hours prior to use, and more preferably immediately prior to use. When carrying out the preparation, a reagent, a solvent, preparation equipment, etc. that are normally available in a place of preparation may be used as appropriate.

The present invention therefore also relates to a preparation kit for the carrier or the composition, the kit including one or more containers containing singly or in combination a targeting agent, and/or a substance to be carried, and/or a carrier-constituting substance other than the targeting agent, and also to a constituent element necessary for the carrier or the composition provided in the form of such a kit. The kit of the present invention may contain, in addition to the above, instructions, an electronic recording medium such as a CD or DVD related to a process for preparing the targeting agent, the carrier, and the composition of the present invention, or an administration method, etc. Furthermore, the kit of the present invention may include all of the constituent elements for completing the targeting agent, the carrier, or the composition of the present invention, but need not always include all of the constituent elements. Therefore, the kit of the present invention need not include a reagent or a solvent that is normally available at a place of medical treatment, an experimental facility, etc. such as, for example, sterile water, physiological saline, or a glucose solution.

The present invention further relates to a method for controlling the activity or growth of a cancer cell or treating a cancer, and a method for controlling the activity or growth of a CAF or treating a cancer in which CAF is involved, the method including administering an effective amount of the composition to a subject that requires it. The effective amount referred to here is, in a method for treating a cancer, for example, an amount that suppresses the onset of a cancer, alleviates the symptoms, or delays or stops progression of the cancer, and is preferably an amount that prevents the onset of a cancer or cures a cancer. It is also preferably an amount that does not cause an adverse effect that exceeds the benefit from administration. Such an amount may be determined as appropriate by an in vitro test using cultured cells or by a test in a model animal such as a mouse, a rat, a dog, or a pig, and such test methods are well known to a person skilled in the art. Moreover, the dose of the targeting agent contained in the carrier and the dose of the drug used in the method of the present invention are known to a person skilled in the art, or may be determined as appropriate by the above-mentioned test, etc.

One embodiment of the cancer treatment method of the present invention involves administering the anticancer composition that includes a targeting agent or a carrier and a drug controlling the activity or growth of a cancer cell, and directly delivering the drug to the cancer cell, thus treating the cancer. Another embodiment of the cancer treatment method of the present invention involves administering the anticancer composition that includes a targeting agent or a carrier and a drug controlling the activity or growth of a CAF, and delivering the drug to a CAF so as to control the activity or growth thereof, thus indirectly treating the cancer. Yet another embodiment of the cancer treatment method of the present invention includes administering the anticancer composition that includes a targeting agent or a carrier and either one of a drug controlling the activity or growth of a cancer cell and a drug controlling the activity or growth of a CAF, or both thereof, and delivering the drug controlling the activity or growth of a cancer cell to a cancer cell and the drug controlling the activity or growth of a CAF to a CAF respectively, thus treating the cancer via two routes. In this embodiment, the drug controlling the activity or growth of a cancer cell and the drug controlling the activity or growth of a CAF may be identical to each other or different from each other.

In the method of the present invention, the specific dose of the composition administered may be determined while taking into consideration various conditions with respect to a subject that requires the treatment, such as for example the severity of the symptoms, general health condition of the subject, age, weight, gender of the subject, diet, the timing and frequency of administration, a medicine used in combination, reaction to the treatment, compliance with the treatment, etc.

As the administration route, there are various routes including both oral and parenteral administrations, and examples thereof include oral, intravenous, intramuscular, subcutaneous, local, rectal, intraarterial, intraportal, intraventricular, transmucosal, percutaneous, intranasal, intraperitoneal, intratumoral, intrapulmonary, and intrauterine routes.

The frequency of administration depends on the properties of the composition used and the above-mentioned condition of the subject, and may be a plurality of times per day (that is, 2, 3, 4, 5, or more times per day), once a day, every few days (that is, every 2, 3, 4, 5, 6, or 7 days, etc.), a few times per week (e.g. 2, 3, 4 times, etc. per week), every other week, or every few weeks (that is, every 2, 3, 4 weeks, etc.).

In the method of the present invention, the term 'subject' means any living individual, preferably an animal, more preferably a mammal, and yet more preferably a human individual. In the present invention, the subject may be healthy or affected by some disorder, and when treatment of a cancer is intended, it typically means a subject affected by a cancer or having a risk of being affected.

Furthermore, the term 'treatment' includes all types of medically acceptable preventive and/or therapeutic intervention for the purpose of the cure, temporary remission, or prevention of a disorder. For example, the term 'treatment' includes medically acceptable intervention for various purposes, including delaying or stopping the progression of a cancer, involution or disappearance of lesions, prevention of onset of a cancer, and prevention of recurrence.

The present invention also relates to a method for delivering a drug to a cancer cell and/or a CAF, utilizing the above carrier. This method includes, but is not limited to, for example, a step of supporting a substance to be carried on the carrier, and a step of administering or adding the carrier having the substance to be carried supported thereon to a living being or a medium, for example a culture medium, containing a cancer cell and/or a CAF. These steps may be achieved as appropriate in accordance with any known method or a method described in the present specification, etc. The above delivery method may be combined with another delivery method, for example, a delivery method targeted at an organ in which a cancer cell and/or a CAF is/are present. Moreover, the above method includes a mode carried out in vitro and a mode in which a cancer cell and/or a CAF inside the body is/are targeted.

The present invention is explained more specifically by reference to Examples below, but the scope of the present invention is not limited by these Examples.

EXAMPLE 1

Separation of CAFs

Cancer tissue or peripheral normal tissue (normal tissue separated from a site spaced from cancer tissue by at least 2 cm) removed from a colon cancer patient was finely cut into 1×1×1 mm, then centrifugally washed with PBS twice, and the pellets were cultured in a culture liquid (DMEM (Dulbecco's Modified Eagle Medium) containing collagenase type I (225 U/ml), hyaluronidase (125 U/ml), 10% FBS (fetal bovine serum), streptomycin/penicillin) for 24 hours. Subsequently, the supernatant was aspirated, and culturing was continued after changing the liquid culture for 10% FBS/DMEM. When the cultured cells were immunostained with an FITC labeled antibody with respect to α-SMA, which is a marker for CAFs, and vimentin, which is a marker for mesenchymal cells, α-SMA was detected only in cancer tissue-derived cells, and it was confirmed that these cells were CAFs (see FIG. 1). Vimentin was positive for cells derived from either tissue, and desmin, which is a marker for epithelial cells, was negative.

EXAMPLE 2

CAF Tumor Growth Activity

Figure 2:
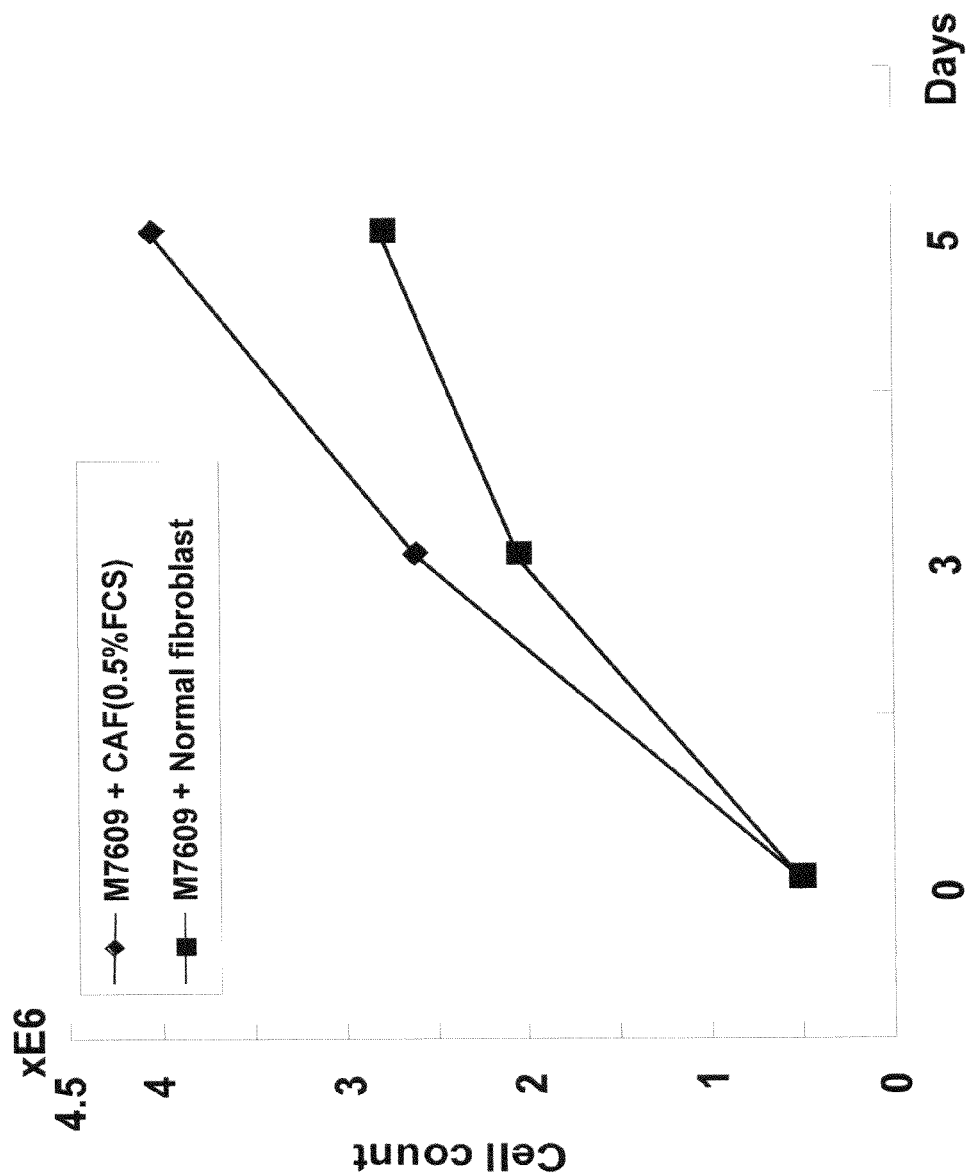
FIG. 2 is a graph showing change in the number of cancer cells when cancer cells and CAFs or normal fibroblasts are cocultured.

A 6-well plate was seeded with CAFs or normal fibroblasts obtained in Example 1 at a density of $1\times10^5$ cells/well and cultured with 10% FBS/DMEM, the liquid culture was replaced with 0.5% FBS/DMEM in a confluent state on the third day, and the liquid culture was seeded with colon cancer cell line M7609 cells ($2\times10^5$ cells), and coculturing was carried out for 7 days. The number of M7609 cells was counted with a Coulter counter (Beckman) at 0 days and on the 3rd and 5th days. The results are given in FIG. 2. This shows that CAFs promote the growth of cancer cells.

EXAMPLE 3

Preparation of siRNA

Three types of siRNA targeted at gp46 (GenBank Accession No. M69246), which is a rat homologue of human HSP47, and a random siRNA control were purchased from Hokkaido System Science Co., Ltd. Each siRNA consists of 27 bases overhanging on the 3' side, and the sequences are as follows.

```
Sequence A:
                              (sense, SEQ ID NO: 1)
5'-GUUCCACCAUAAGAUGGUAGACAACAG-3'

(antisense, SEQ ID NO: 2)
5'-GUUGUCUACCAUCUUAUGGUGGAACAU-3'

Sequence B:
                              (sense, SEQ ID NO: 3)
5'-CCACAAGUUUUAUAUCCAAUCUAGCAG-3'

(antisense, SEQ ID NO: 4)
5'-GCUAGAUUGGAUAUAAAACUUGUGGAU-3'

Sequence C:
                              (sense, SEQ ID NO: 5)
5'-CUAGAGCCAUUACAUUACAUUGACAAG-3'

(antisense, SEQ ID NO: 6)
5'-UGUCAAUGUAAUGUAAUGGCUCUAGAU-3'

Random siRNA:
                              (sense, SEQ ID NO: 7)
5'-CGAUUCGCUAGACCGGCUUCAUUGCAG-3'

(antisense, SEQ ID NO: 8)
5'-GCAAUGAAGCCGGUCUAGCGAAUCGAU-3'
```

Furthermore, siRNA labeled on the 5' side with the fluorescent dye 6'-carboxyfluorescein (6-FAM) was also prepared.

EXAMPLE 4

Preparation of siRNA-Containing VA-Bound Liposome

As a liposome, a cationic liposome containing DC-6-14, cholesterol, and DOPE at a molar ratio of 4:3:3 (Lipotrust, Hokkaido System Science Co., Ltd.) was used. 10 nmol of liposome and 20 nmol of all-trans retinol (hereinafter, referred to as 'VA') were mixed in DMSO using a 1.5 mL tube, then dissolved in chloroform, evaporated once, and then suspended in PBS. Subsequently, the siRNA (10 μg/mL) obtained in Example 3 and the liposome suspension were mixed at a ratio of 1:1 (w/w). Free VA and siRNA contained in the liposome suspension thus obtained were removed by a micropartition system (Sartorion VIVASPIN 5000MWCO PES), thus giving an siRNA-containing VA-bound liposome (VA-lip-siRNA). The amount of VA added and the amount of VA contained in the purified liposome were measured by HPLC, and when the proportion of VA bound to the liposome was examined, it was found that the majority of the VA (95.6±0.42%) was bound to the liposome. Furthermore, when the efficiency of uptake of siRNA into the liposome was measured by RiboGreen assay (Molecular Probes), it was 94.4±3.0%, which is high. Part of the VA was exposed on the surface of the liposome.

In the same manner as above, siRNA-containing liposome (lip-siRNA) and VA-bound liposome (VA-lip) were prepared.

EXAMPLE 5

Uptake of VA-Lip-siRNA

Figure 3:
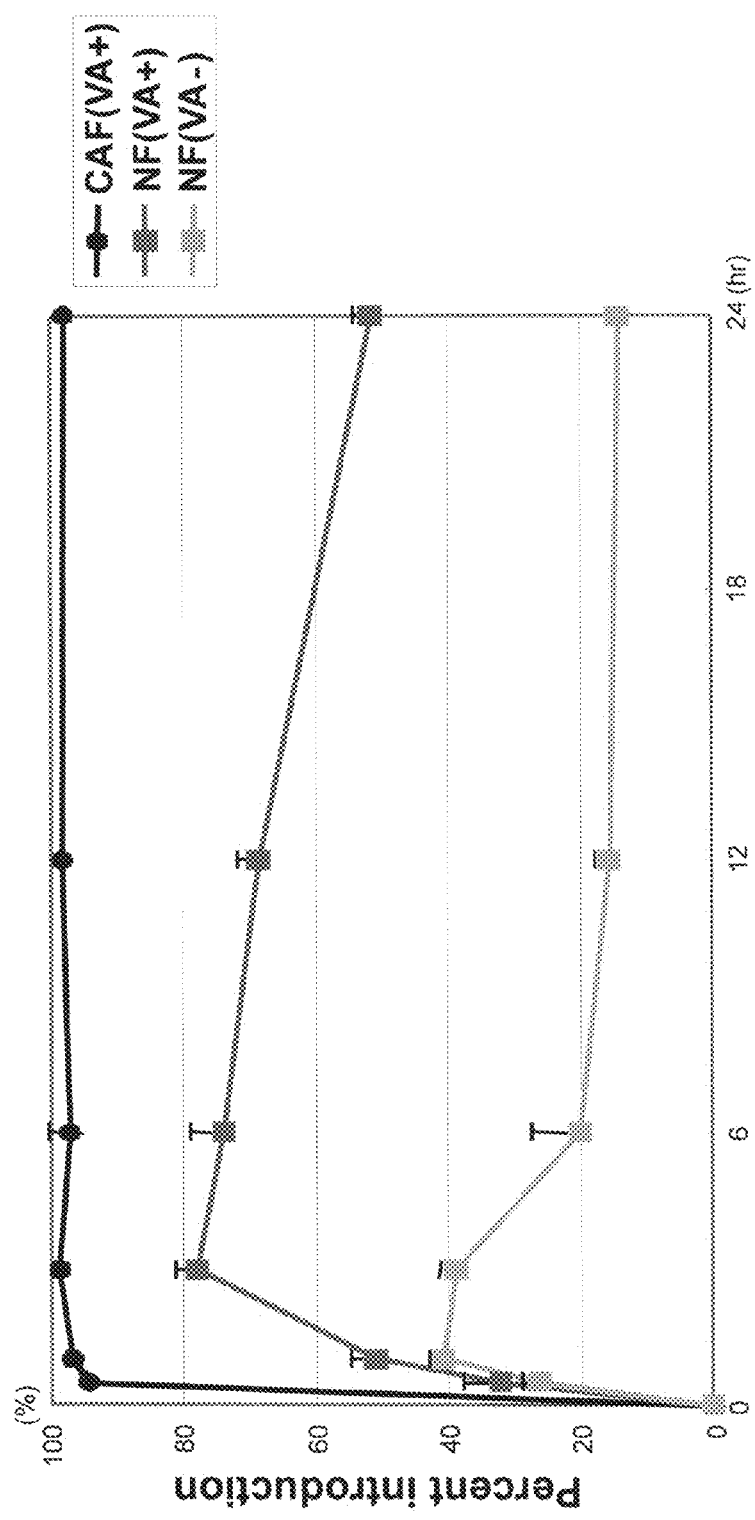
FIG. 3 is a graph in which the percentage introduction of siRNA to CAFs or normal fibroblasts when siRNA is delivered by various liposomes is compared over time.
Figure 4:
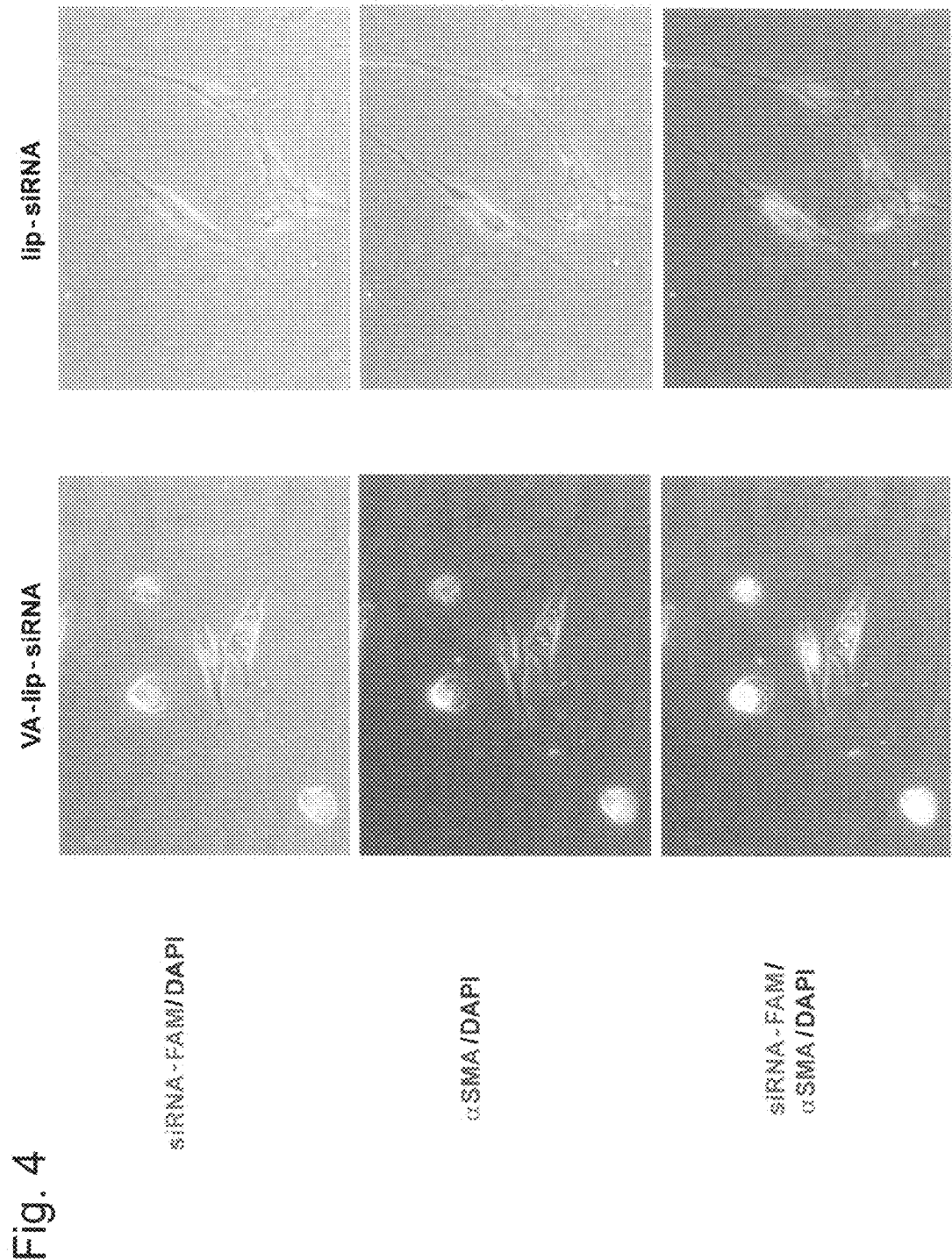
FIG. 4 is a photographic diagram showing the localization of siRNA in CAFs that have been reacted with VA-lip-siRNA or lip-siRNA.
Figure 5:
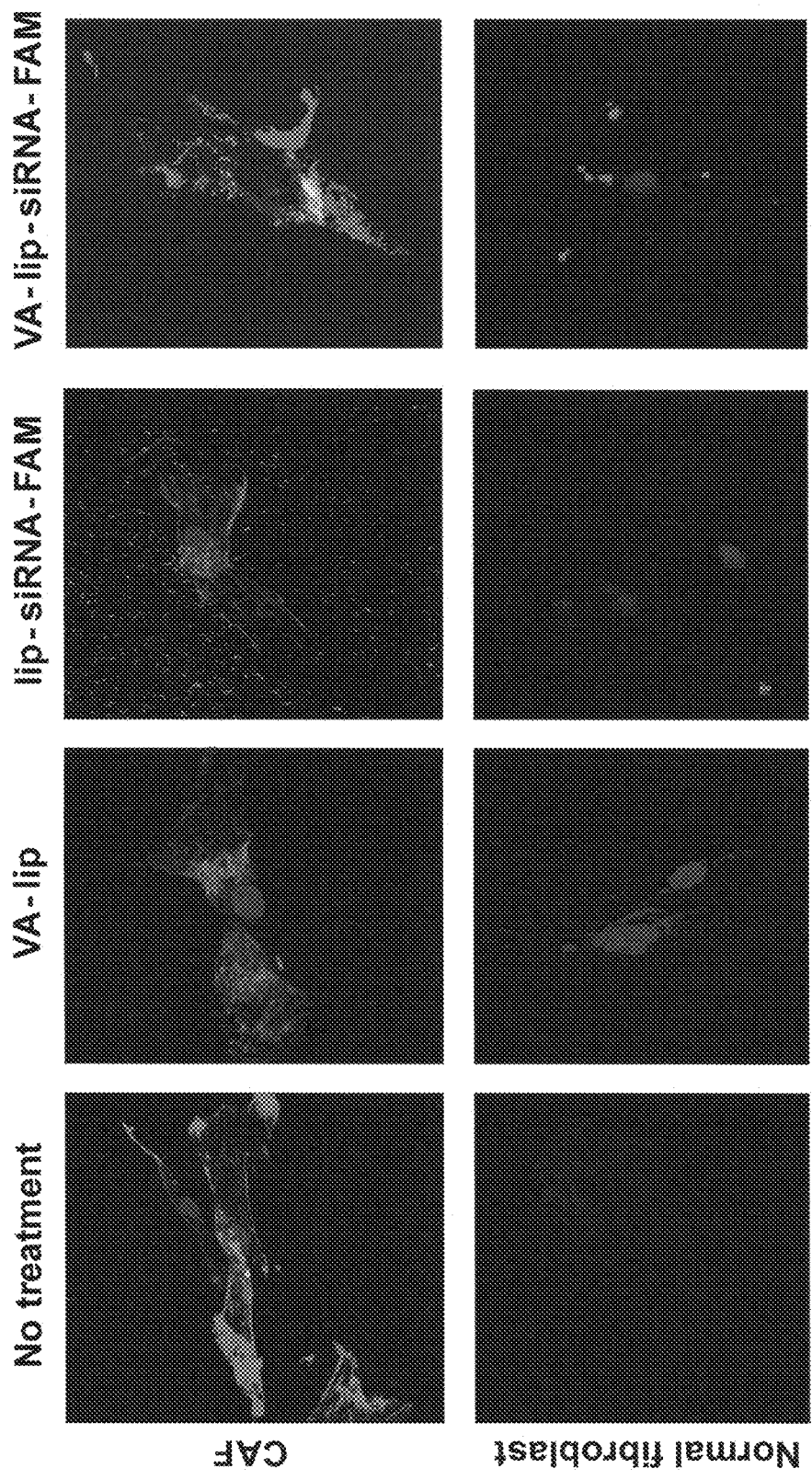
FIG. 5 is a photographic diagram showing the localization of siRNA in CAFs and normal fibroblasts that have been reacted with VA-lip-siRNA, lip-siRNA, or VA-lip.

A 6-well plate was seeded with CAFs or normal fibroblasts at a density of $5\times10^5$ cells/well, and culturing was carried out in 10% FBS/DMEM. After 2 days it was washed with serum-free medium in a subconfluent state, and the medium was replaced with serum-containing OPTI-MEM. Subsequently, the liposome suspension containing siRNA (final concentration 50 pmol/mL) obtained in Example 4 was added to the medium, and reacted at 37° C. for 24 hours. When the VA-bound liposome was added, the final concentration of VA was adjusted to 40 nmol/mL. Furthermore, as siRNA, 6-FAM labeled random siRNA was used. 0, 0.5, 1, 3, 6, 12, 18, and 24 hours after the reaction was started, the uptake of siRNA into each cell species was evaluated by flow cytometry (FIG. 3). After the reaction was complete, the cells were stained with DAPI (Molecular Probe) and Cy3-labeled anti α-SMA antibody, and the localization of siRNA was analyzed (FIGS. 4 to 5).

As is clear from FIG. 3, it has been found that when the VA-containing carrier was used, the rate of transfer of siRNA into CAFs was at least 3 times the transfer rate into normal fibroblasts, the uptake by CAFs when 24 hours had elapsed was maintained at almost 100%, and the specificity and transfer efficiency were very high. Furthermore, FIG. 4 shows a representative field of vision used in evaluating the localization of siRNA, and according to this, when the VA-bound liposome (VA-lip-siRNA-FAM) was used, siRNA was incorporated into all of the CAFs in the field of vision, but when the liposome containing no VA (lip-siRNA-FAM) was used, siRNA was incorporated into only 1 CAF among 5 CAFs in the field of vision. Moreover, FIG. 5 shows that siRNA is not localized within the CAF cell for the liposome containing no VA (lip-siRNA-FAM), but most of the siRNA is localized within the cell for the VA-bound liposome (VA-lip-siRNA-FAM), and high efficiency transfer of siRNA into the CAF is VA dependent. From the above results, it is clear that the VA-containing carrier specifically and markedly promotes the uptake of a substance into CAF.

EXAMPLE 6

Uptake of VA-Lip-DNR

Uptake by CAFs was examined using VA-bound liposome containing daunorubicin (DNR) instead of siRNA.

Liposome encapsulated DNR (lip-DNR, DaunoXome®, hereinafter also called liposomal DNR) and VA were mixed in DMSO at a molar ratio of liposome:VA=1:2, then dissolved in chloroform, evaporated once, and then suspended in PBS. Free VA contained in the liposome suspension thus obtained was removed by a micropartition system (Sartorion VIVASPIN 5000MWCO PES), thus giving DNR-containing VA-bound liposome (VA-lip-DNR, hereinafter also called VA-bound liposomal DNR). The amount of VA added and the amount of VA contained in the purified liposome were measured by HPLC, and when the proportion of VA bound to the liposome was examined, it was found that the majority of the VA (98%) was bound to the liposome. Part of the VA was exposed on the surface of the liposome. In DaunoXome®, daunorubicin citrate is encapsulated in a liposome formed from distearoyl phosphatidylcholine (DSPC) and cholesterol (Chol), and the molar ratio of DSPC:Chol:daunorubicin citrate is 10:5:1.

A chamber slide was seeded with the CAFs obtained in Example 1, normal fibroblasts, or commercial fibroblasts (skin fibroblast, Cells System, product No. CS-2FO-101) respectively at a density of $2 \times 10^4$ cells/chamber, cultured with 10% FBS/DMEM overnight, then washed with serum-free medium once in a subconfluent state, and the medium was replaced with serum-containing OPTI-MEM. Subsequently, a liposome suspension containing lip-DNR or the VA-lip-DNR obtained above at 5 µg/mL as a DaunoXome® concentration was added to medium and reacted at 37° C. Furthermore, nuclei were stained with DAPI. The localization of DNR, which exhibited a red color, was examined under a fluorescence microscope before the reaction started (0 min), and 5 minutes, 15 minutes, and 30 minutes after the reaction started. The results are given in FIGS. 6 to 9.

Figure 6:
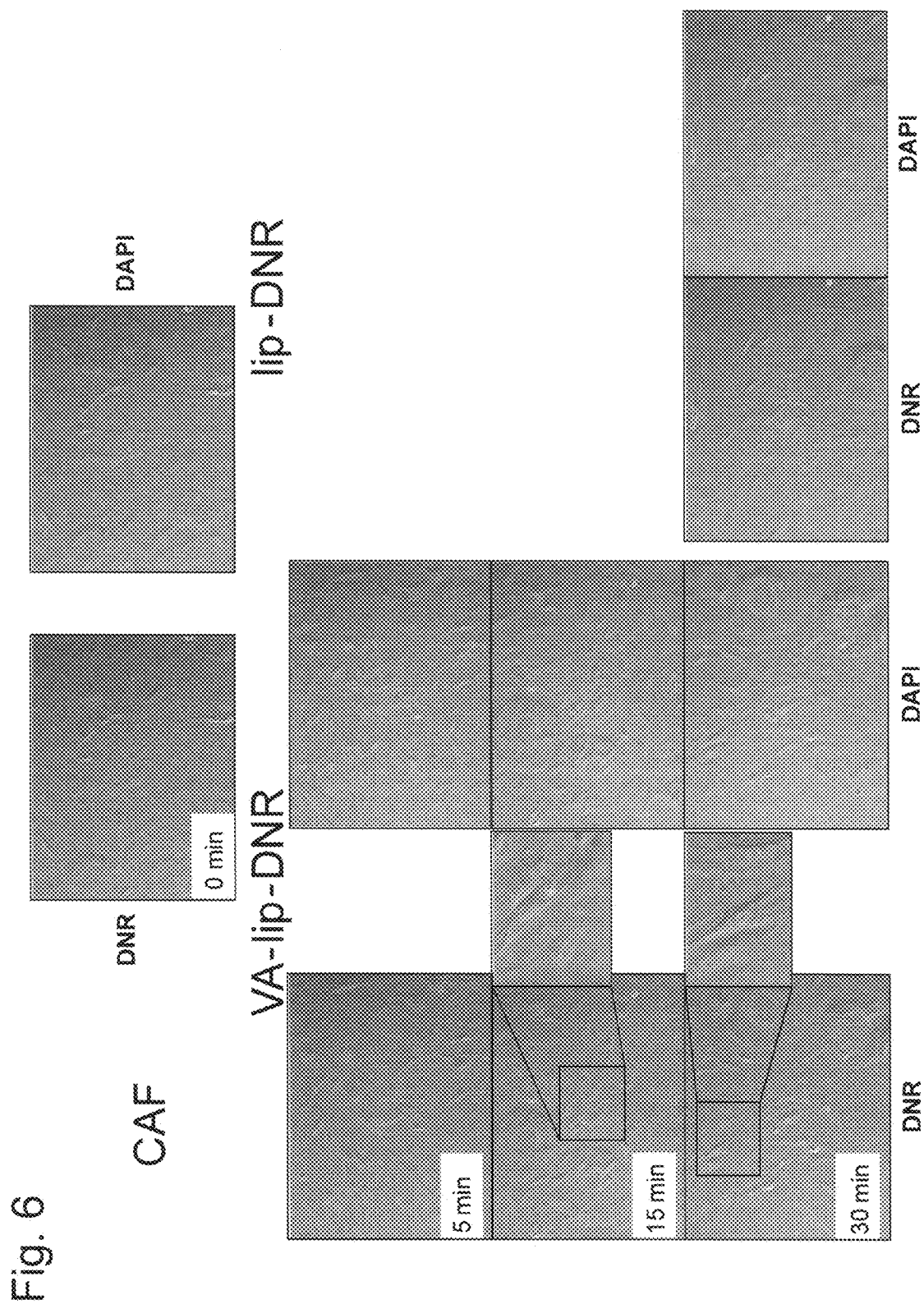
FIG. 6 is a photographic diagram showing the localization of DNR in CAFs that have been reacted with VA-lip-DNR or lip-DNR. The numbers in the diagram show elapsed time (min) from the start of the reaction. The magnification is 200 times (400 times for enlarged images).
Figure 7:
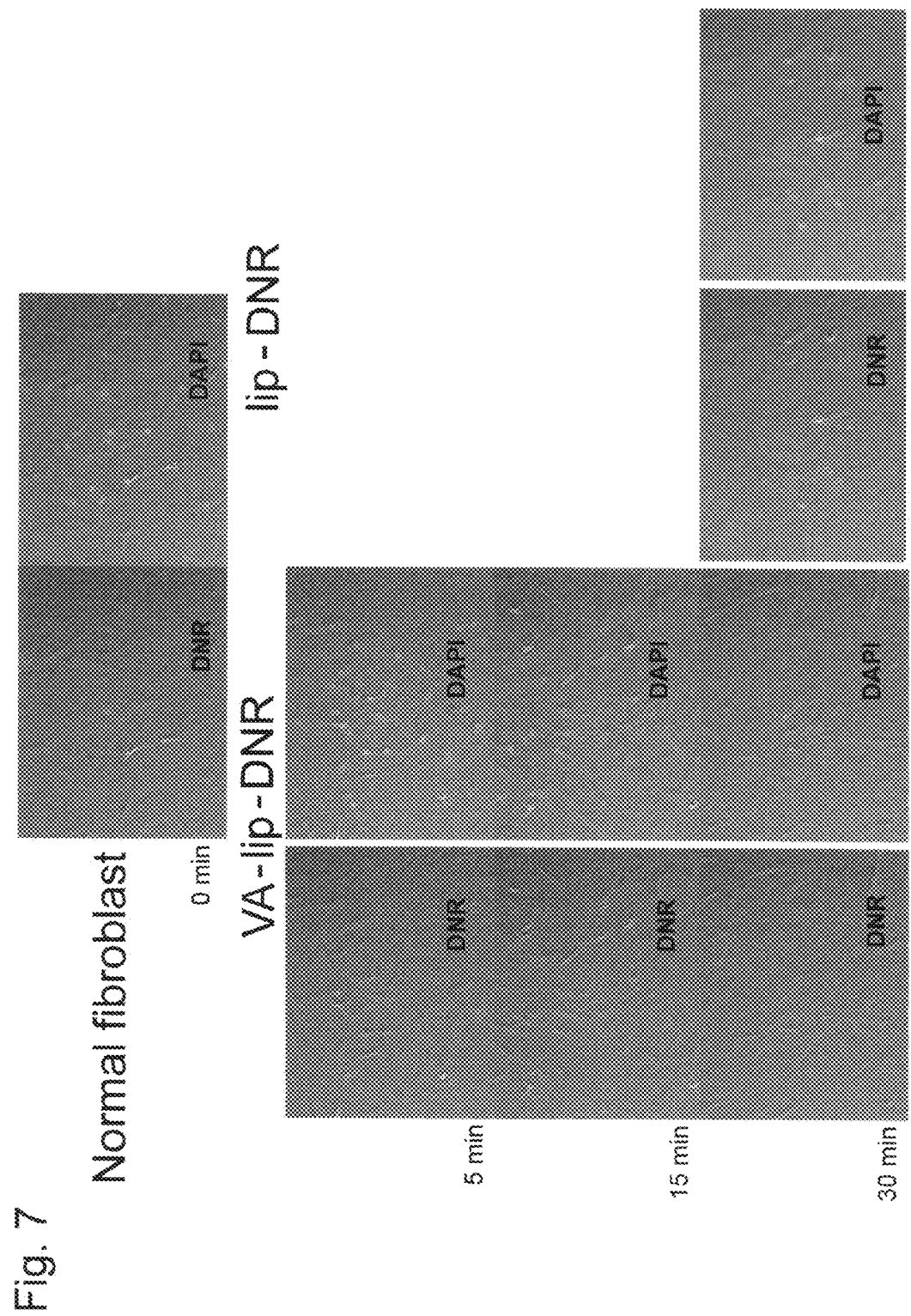
FIG. 7 is a photographic diagram showing the localization of DNR in normal fibroblasts that have been reacted with VA-lip-DNR or lip-DNR. The numbers in the diagram show elapsed time (min) from the start of the reaction. The magnification is 200 times.
Figure 8:
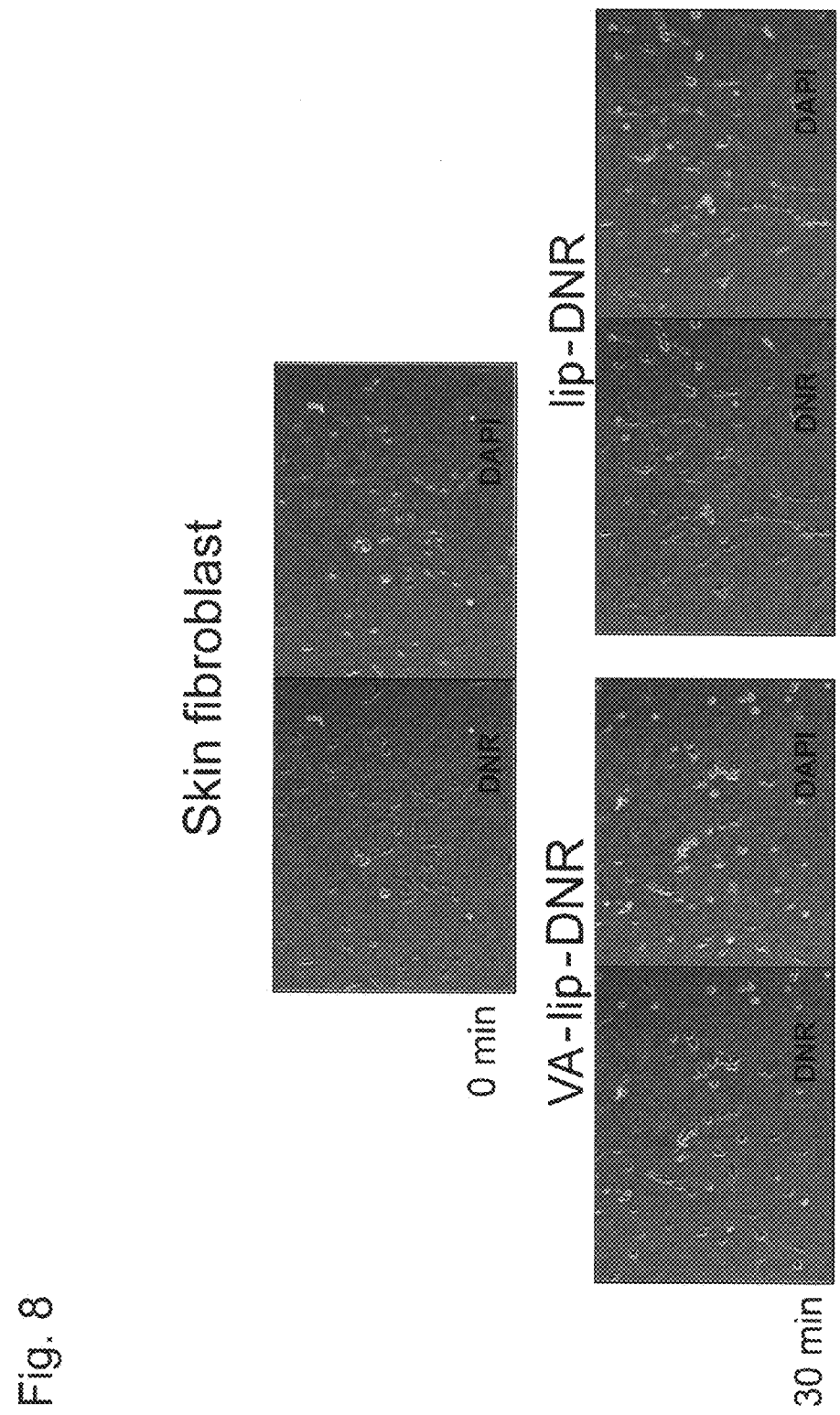
FIG. 8 is a photographic diagram showing the localization of DNR in skin fibroblasts that have been reacted with VA-lip-DNR or lip-DNR. The numbers in the diagram show elapsed time (min) from the start of the reaction. The magnification is 200 times.
Figure 9:
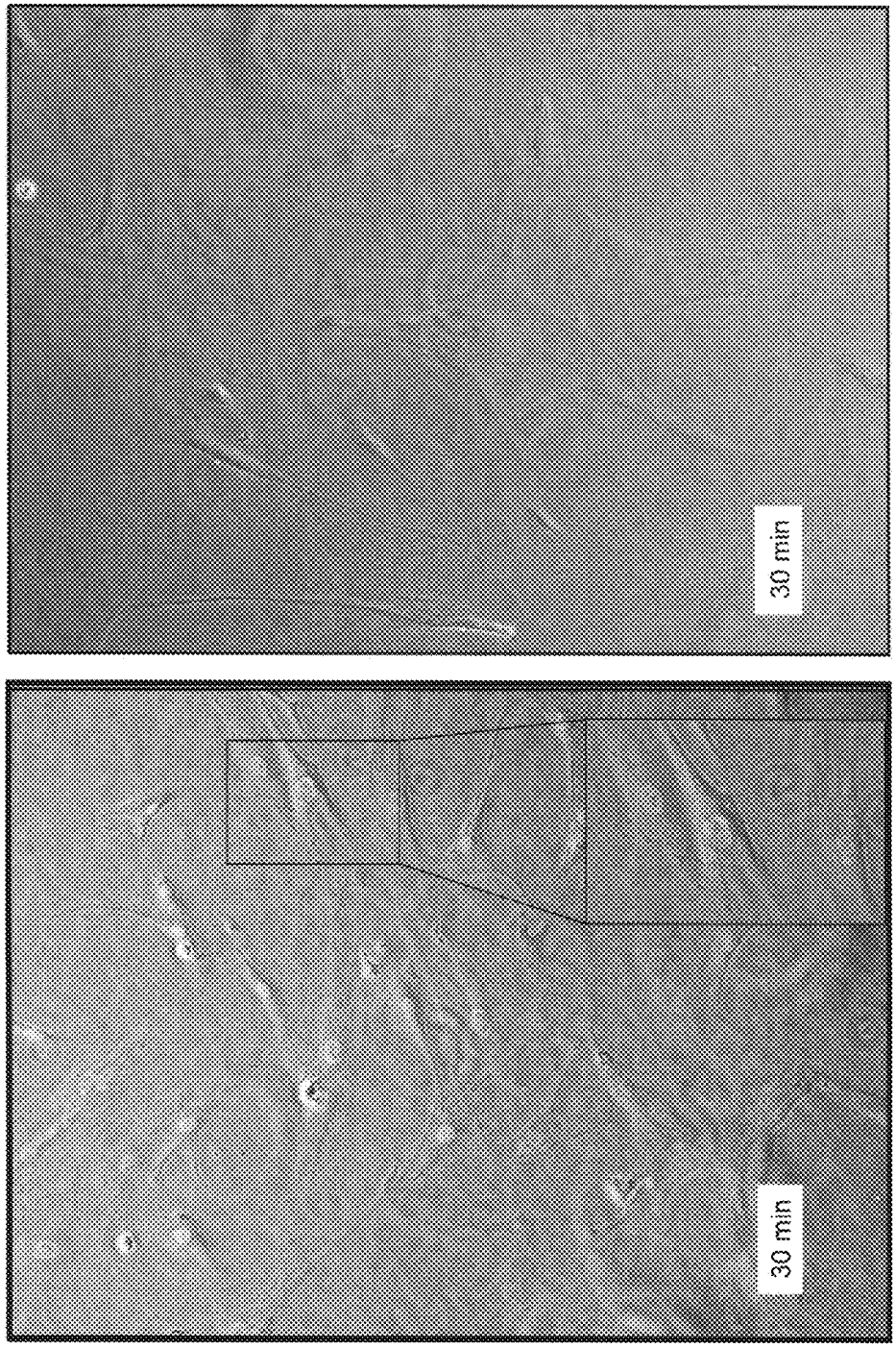
FIG. 9 is a photographic diagram showing the localization of DNR in CAFs that have been reacted with VA-lip-DNR (left) or lip-DNR (right). The magnification is 400 times (800 times for enlarged image).

In CAFs to which VA-lip-DNR was added, a red color was already observed within the cell at 15 minutes after the addition, but in a group to which lip-DNR was added localization of DNR into the cells was not observed (FIGS. 6 and 9). Furthermore, in normal fibroblasts (FIG. 7) and skin fibroblasts (FIG. 8), localization of DNR was not observed either in the group to which VA-lip-DNR was added or in the group to which lip-DNR was added. These results show that the VA-bound carrier causes CAF-specific drug delivery.

EXAMPLE 7

Targeting of the VA Derivative Retinoic Acid (RA) at Cancer Cells and CAFs (1) Cultured Cells CAF cells were established by cloning from a clinical sample of a human cancer patient. HT-1080 human fibrosarcoma cells (fibrosarcoma), and HepG2 human hepatic cancer-derived cells were purchased from American Type Culture Collection. All cells were cultured with a DMEM medium (Sigma Aldrich) to which 10% fetal bovine serum (FBS) was added. They were trypsinized, a 4-well culture slide (BD Falcon #354114) was then seeded therewith at $2 \times 10^5$ cells/mL, and cultured overnight under conditions of 37° C. and 5% $CO_2$.

(2) Preparation of VA-Containing Liposomal Formulation

As a model drug, DaunoXome® (Gilead Sciences, Inc.), which is a liposome encapsulated daunorubicin formulation, was used. DaunoXome® contains the drug daunorubicin at a concentration of 2 mg/mL. 990 µL of 10% FBS-containing DMEM was added to 10 µL of DaunoXome®, thus giving a 20 µg/mL solution. This was mixed with 7.14 µL of all-trans retinol (VA) and all-trans retinoic acid (Retinoic acid, RA) dissolved in dimethylsulfoxide (DMSO) to give 100 mM, thus giving a VA-containing liposomal formulation (VA+) and an RA-containing liposomal formulation (retinoic acid+) respectively. At least part of the VA and the RA was exposed on the surface of the liposome. In addition to these liposomal formulations, as a control group a formulation (VA−), which was a DaunoXome® solution containing no VA or RA, was prepared.

(3) Administration of VA and RA Liposomal Formulations

The medium was removed from the culture slide, and 750 µL of fresh 10% FBS-containing DMEM was added thereto. Except for the culture slide that had no treatment (No treatment), 250 µL of formulation (VA−), which was the DaunoXome® solution containing no VA or RA, the VA− containing liposomal formulation (VA+), and the RA− containing liposomal formulation (retinoic acid+) respectively were added and incubated under conditions of 37° C. and 5% $CO_2$ for 15 minutes. The medium was removed from each of the culture slides, they were washed with 1 mL of PBS twice, subsequently 1 mL of a 4% paraformaldehyde solution (Wako Pure Chemical Industries, Ltd.) was added thereto, and the cells were fixed at room temperature for 5 minutes. The fixing solution was then removed, and the cells were washed with PBS three times. The slide glass was taken out from each culture slide, Prolong Gold (Invitrogen) was added dropwise, and the slide glass was sealed with a cover glass.

(4) Microscopic Examination

Figure 10:
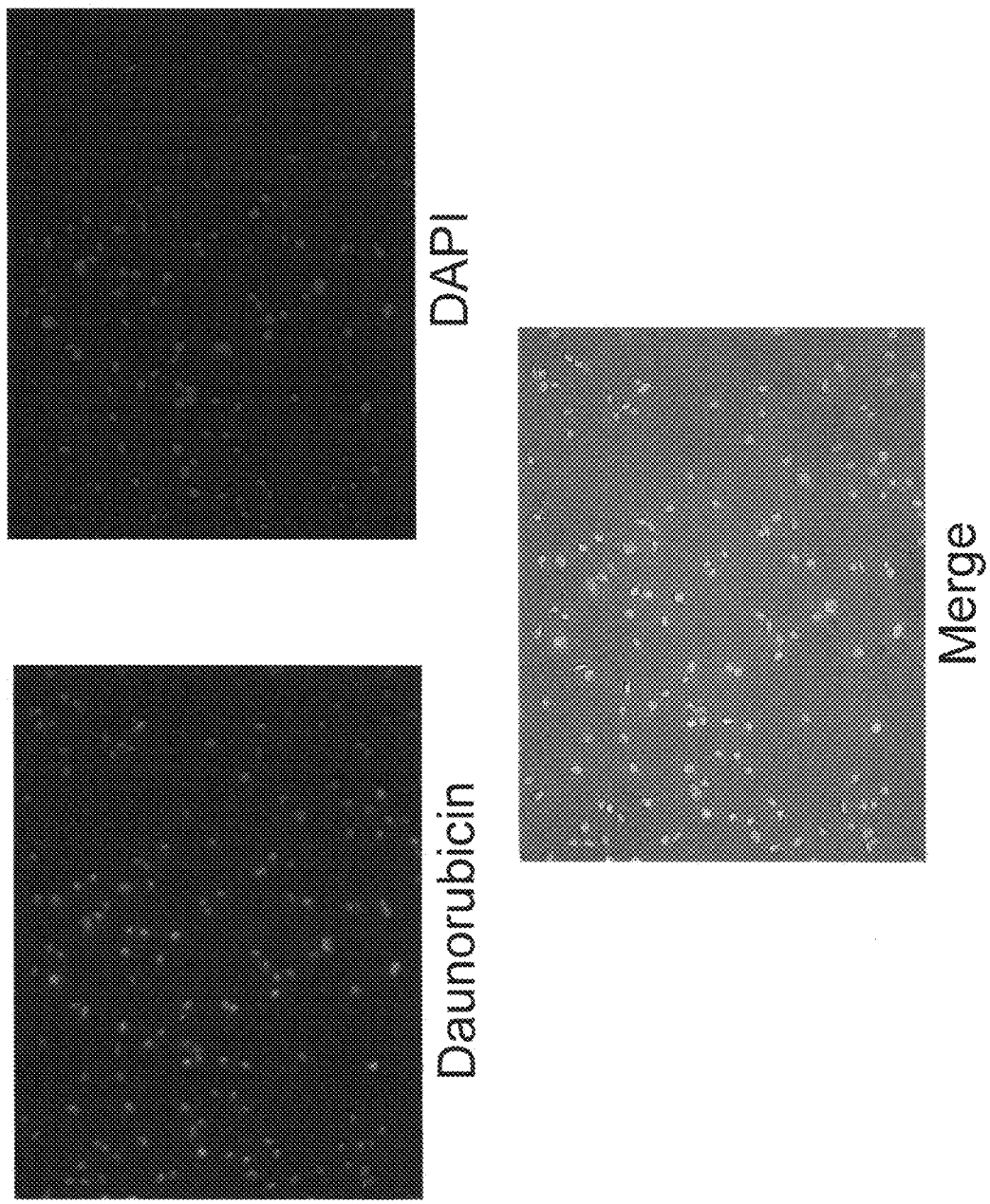
FIG. 10 is a photographic diagram showing daunorubicin emitting red fluorescence under green excitation light (upper left), DAPI (4',6-diamino-2-phenylindole) emitting blue fluorescence under UV excitation light (upper right), and a merged image exhibiting a purple color (lower).

The slide glass was examined using a fluorescence microscope (Keyence BZ8000). It is known that daunorubicin is incorporated into the nucleus of a cell and emits red fluorescence under green excitation light (FIG. 10 upper left). Furthermore, the Prolong Gold used when sealing contains the fluorescent dye DAPI. DAPI binds to the nucleus of a cell and exhibits blue fluorescence under UV excitation light (FIG. 10 upper right). Therefore, in microscopic examination, when there is uptake of a liposomal formulation, both red and blue fluorescence is observed, and as a result a purple color is exhibited when superimposing the two images (FIG. 10 lower). On the other hand, when a liposomal formulation is not incorporated into a cell, only blue fluorescence due to DAPI is detected.

Figure 11:
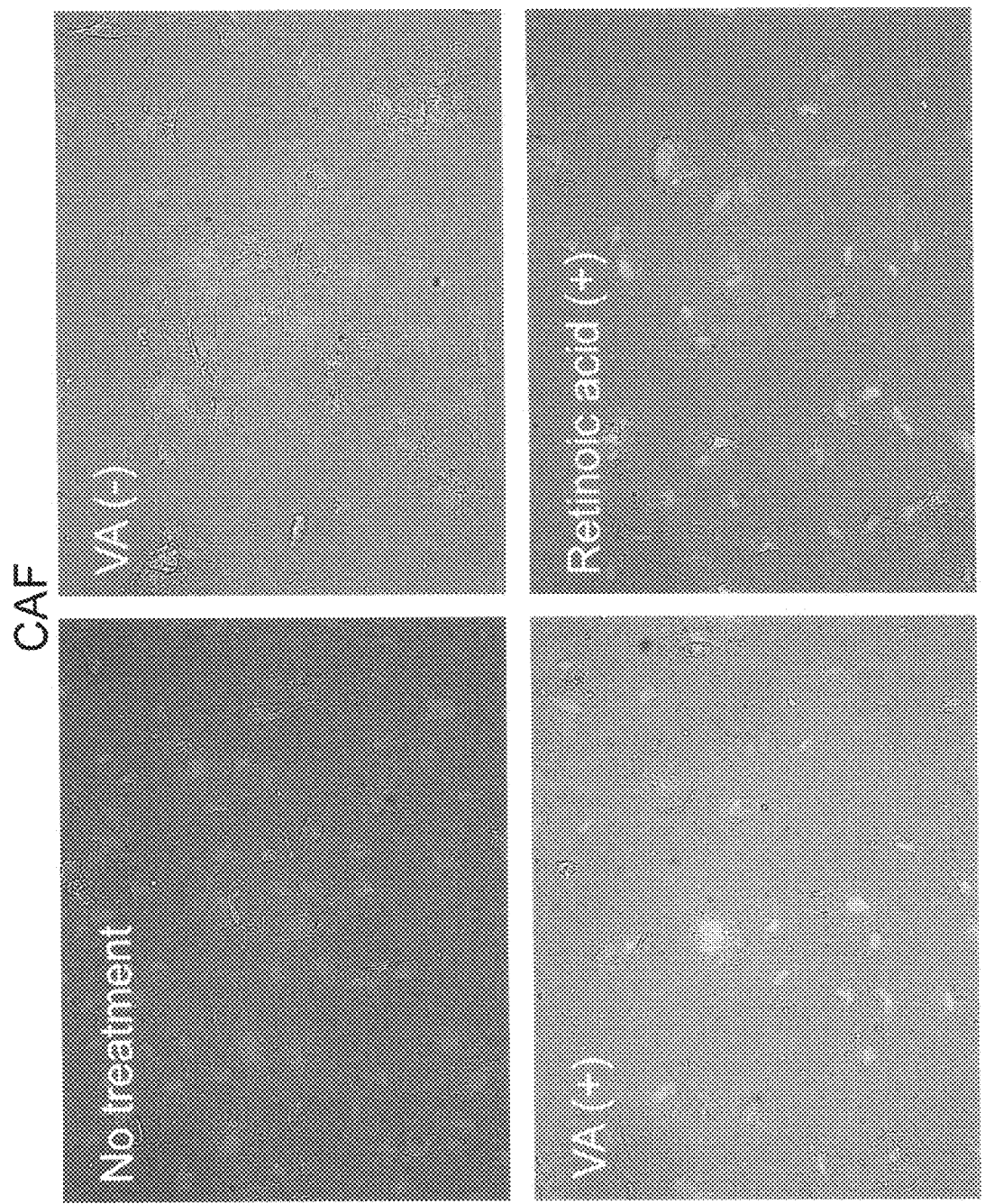
FIG. 11 is a photographic diagram showing the localization of DNR in CAFs that have been either not treated (No treatment: upper left) or reacted with DaunoXome® (VA−: upper right), DaunoXome®+retinol (VA+: lower left), or DaunoXome®+retinoic acid (Retinoic acid+: lower right). The magnification is 400 times.
Figure 12:
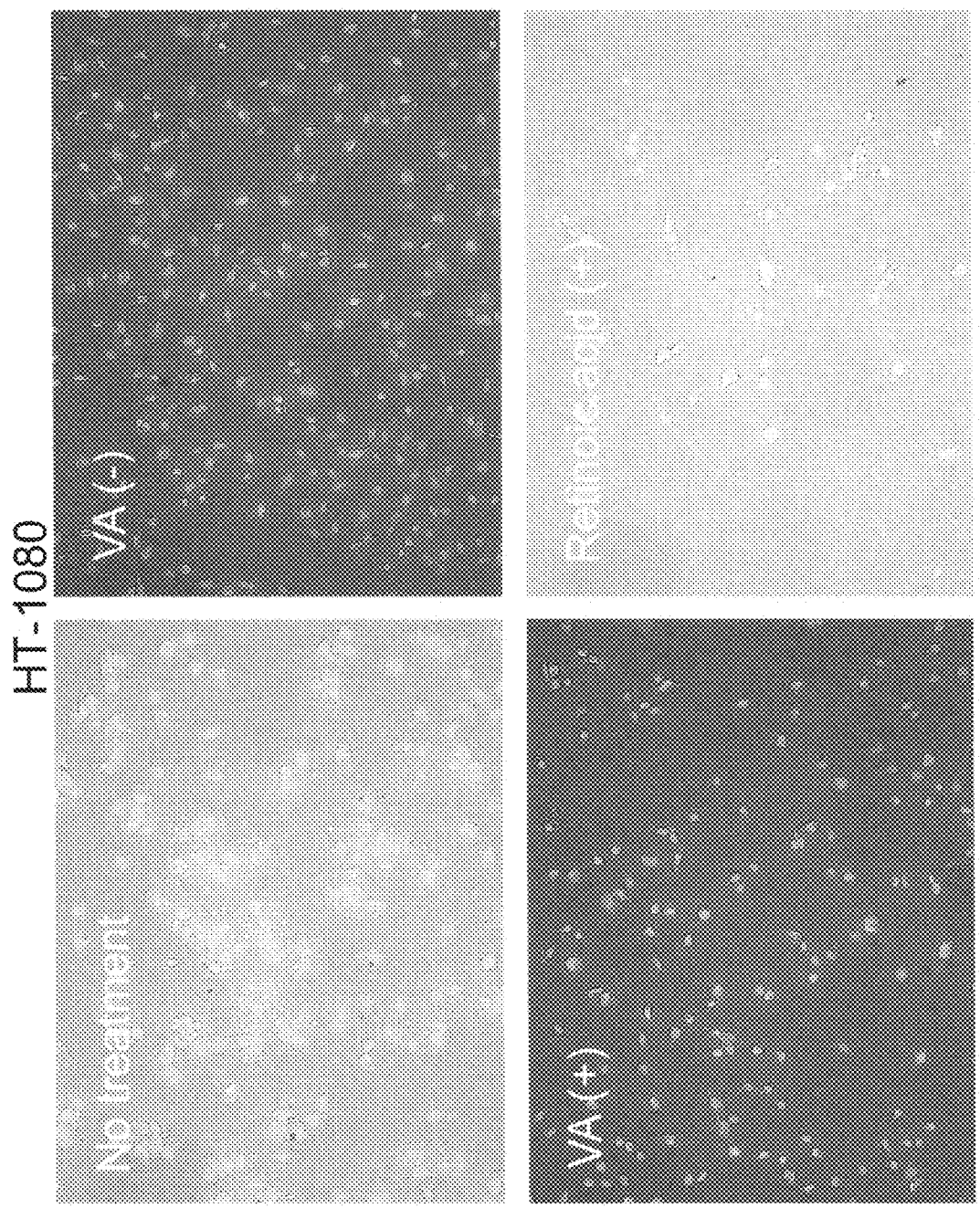
FIG. 12 is a photographic diagram showing the localization of DNR in HT-1080 that has been either not treated (No treatment: upper left) or reacted with DaunoXome® (VA−: upper right), DaunoXome®+retinol (VA+: lower left), or DaunoXome®+retinoic acid (Retinoic acid+: lower right). The magnification is 400 times.
Figure 13:
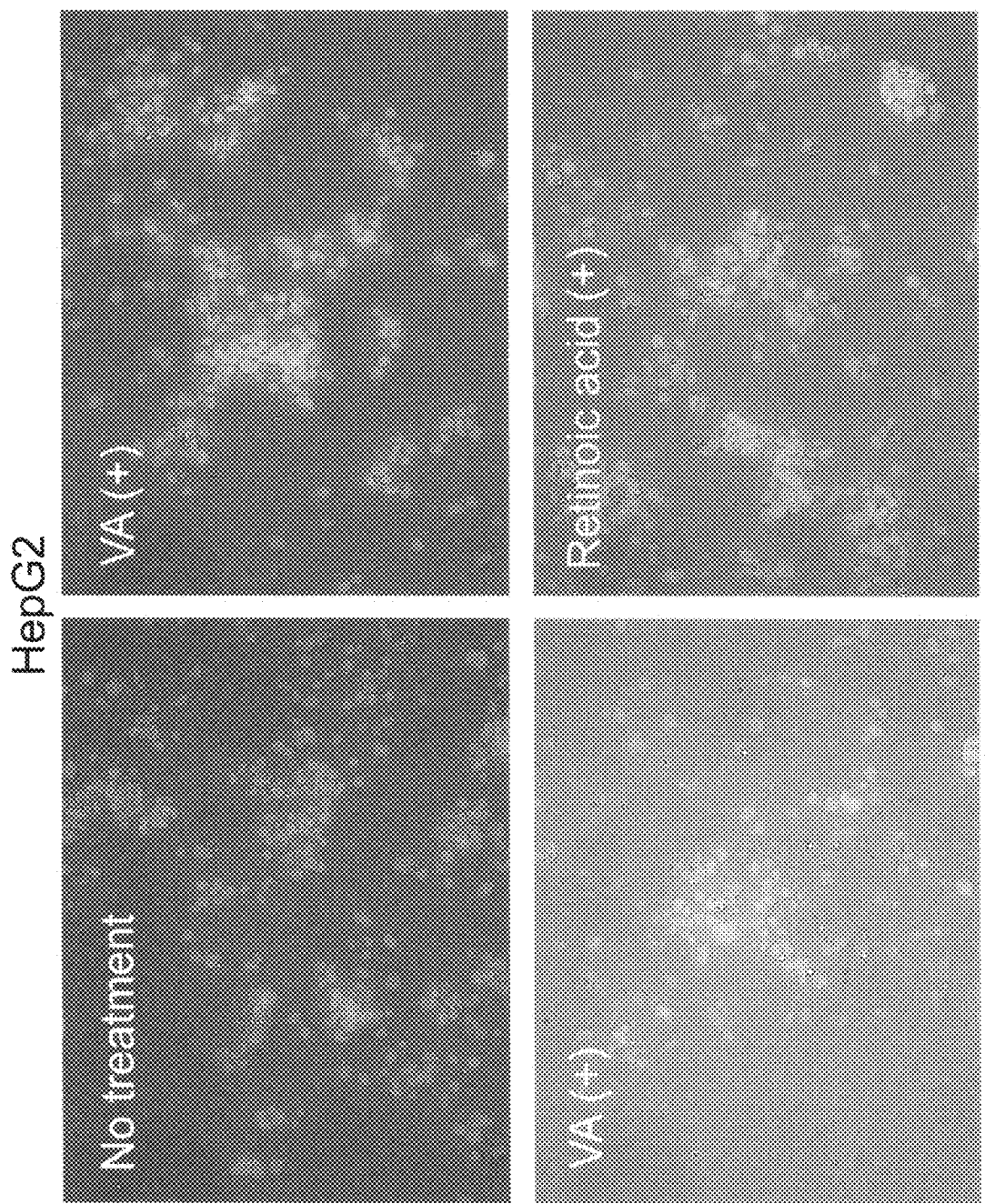
FIG. 13 is a photographic diagram showing the localization of DNR in HepG2 that has been either not treated (No treatment: upper left) or reacted with DaunoXome® (VA−: upper right), DaunoXome®+retinol (VA+: lower left), or DaunoXome®+retinoic acid (Retinoic acid+: lower right). The magnification is 400 times.

The slide glass was examined by a phase contrast microscope and the fluorescence microscope. An image of the slide glass taken by the phase contrast microscope under bright field, an image taken by the fluorescence microscope under green excitation light, and an image taken under UV excitation light were electronically merged (merge). Merged images are shown in FIGS. 11 to 13, and the observation results are shown in Tables 1 to 3. In the tables, + denotes that fluorescence was observed, and − denotes that fluorescence was not observed.

TABLE 1

Uptake of liposomal formulation in CAFs (FIG. 11)

|  | DAPI (blue fluorescence) | Daunorubicin (red fluorescence) |
|---|---|---|
| No treatment (No treatment) | + | − |
| DaunoXome ® (VA−) | + | − |
| DaunoXome ® + retinol (VA+) | + | + |
| DaunoXome ® + retinoic acid (Retinoic acid+) | + | + |

TABLE 2

Uptake of liposomal formulation in HT-1080 (FIG. 12)

|  | DAPI (blue fluorescence) | Daunorubicin (red fluorescence) |
|---|---|---|
| No treatment (No treatment) | + | − |
| DaunoXome ® (VA−) | + | − |
| DaunoXome ® + retinol (VA+) | + | + |
| DaunoXome ® + retinoic acid (Retinoic acid+) | + | + |

TABLE 3

Uptake of liposomal formulation in HepG2 (FIG. 13)

|  | DAPI (blue fluorescence) | Daunorubicin (red fluorescence) |
|---|---|---|
| No treatment (No treatment) | + | − |
| DaunoXome ® (VA−) | + | − |
| DaunoXome ® + retinol (VA+) | + | + |
| DaunoXome ® + retinoic acid (Retinoic acid+) | + | + |

As is clear from these results, the presence of cell nuclei was confirmed for all the slide glasses due to the blue fluorescence of DAPI. The red fluorescence of daunorubicin showed that in the slide glasses employing VA and RA, localization of daunorubicin in cell nuclei was observed even after an incubation of as little as 15 minutes. In contrast thereto, in the slide glass employing no VA or RA, there was no localization of daunorubicin in the cell nucleus. This suggests that a retinoid can be used as a targeting agent to a CAF or a cancer cell.

EXAMPLE 8

CAF-Specific Growth Inhibition by VA-Bound Liposome Encapsulated Drug

Figure 14:
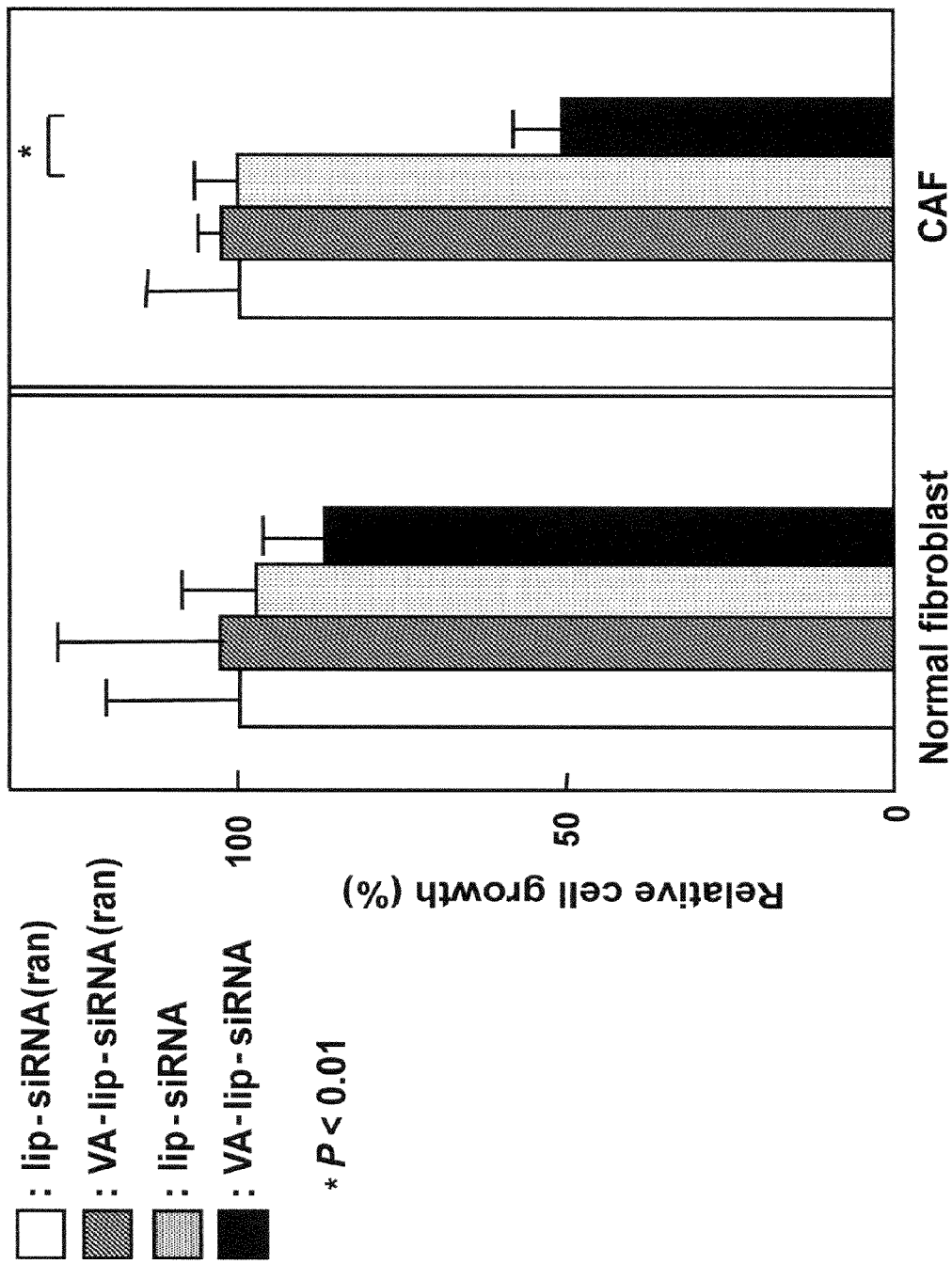
FIG. 14 is a graph showing the result of evaluation of the growth inhibitory activity of VA-lip-siRNA toward CAFs or normal fibroblasts. The ordinate denotes the percentage viable cell count after treatment when the viable cell count prior to treatment is 100.
Figure 15:
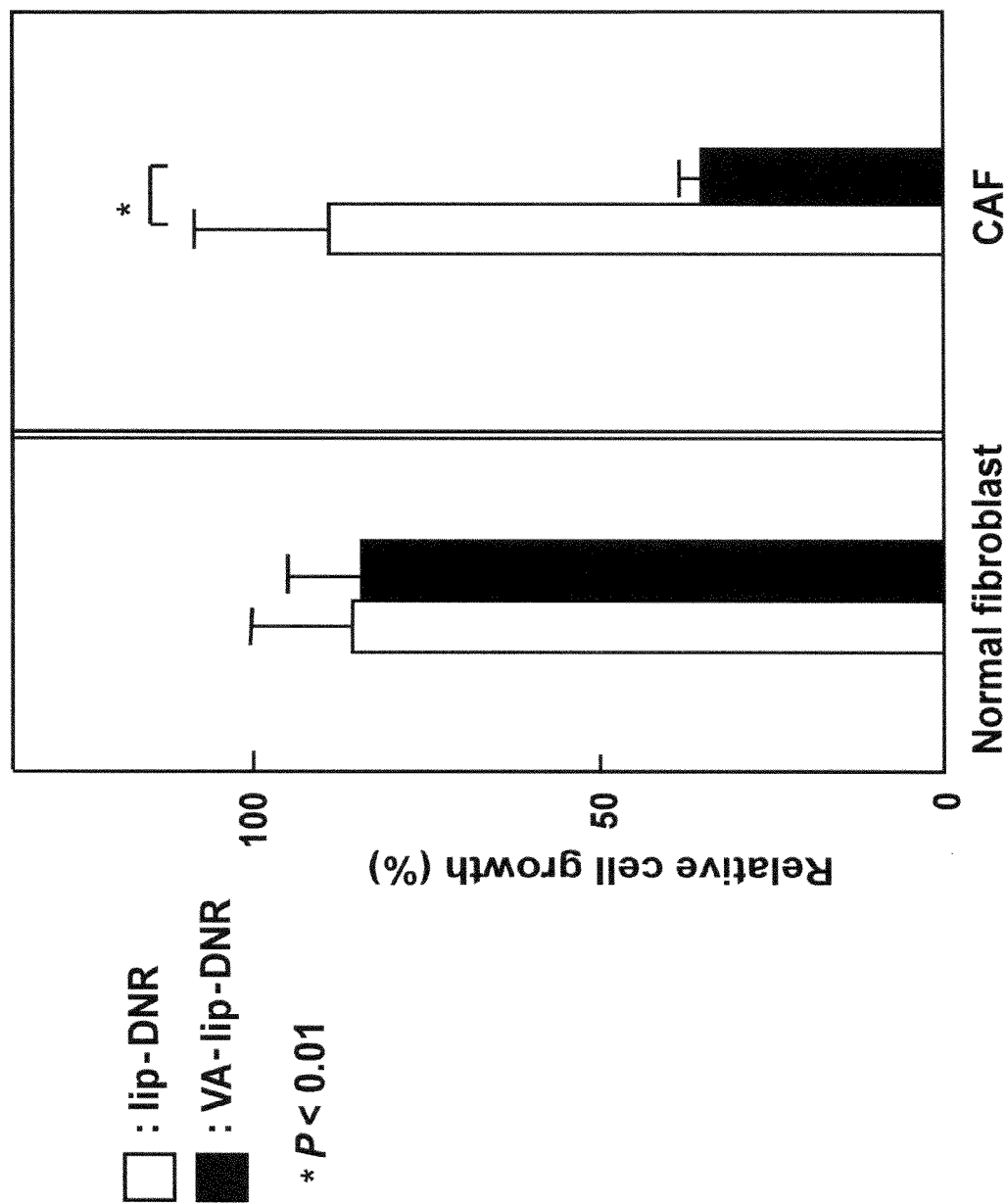
FIG. 15 is a graph showing the result of evaluation of the growth inhibitory activity of VA-lip-DNR toward CAFs or normal fibroblasts. The ordinate denotes the percentage viable cell count after treatment when the viable cell count prior to treatment is 100.

The CAF growth inhibitory activity of VA-bound liposome containing siRNA toward gp46 or DNR was examined.
(1) Growth Inhibition by VA-Lip-siRNA
As the siRNA, sequence A described in Example 3 was used. A 24-well dish was seeded with CAFs and normal fibroblasts respectively at 1×10$^4$ cells and cultured with 10% FBS/DMEM for 24 hours, VA-lip-siRNA was added at a final concentration of 50 pmol/mL, incubation was carried out for 1 hour, and subsequently the cells were washed. The viable cell count was measured by the WST-1 method after culturing with 10% FBS/DMEM for 48 hours. As a control, lip-siRNA- and random siRNA-containing VA-bound and nonbound liposomes (VA-lip-siRNA (ran) and lip-siRNA (ran)) were used, and evaluation of significant difference was carried out by the U test. The results are given in FIG. 14. From this figure, it can be seen that in CAFs to which VA-lip-siRNA was added the viable cell count greatly decreased to less than 50% of that prior to the treatment, but in the other treatment groups there was hardly any change in the viable cell count.
(2) Growth Inhibition by VA-Lip-DNR
A 96-well dish was seeded with CAFs or normal fibroblasts respectively at 2×10$^3$ cells, and cultured with 10% FBS/DMEM for 24 hours, subsequently the VA-lip-DNR obtained in Example 6 or lip-DNR was added at a final DaunoXome® concentration of 5 μg/mL and after exposing for 15 minutes, the cells were washed. Culturing was carried out with 10% FBS/DMEM for 24 hours, and the viable cell count was measured by the WST-1 method. Evaluation of significant difference was carried out by the U test. The results are shown in FIG. 15. From this figure, it can be seen that in CAFs to which VA-lip-DNR was added the viable cell count greatly decreased to about 40% of that prior to the treatment, but in the CAFs to which lip-DNR was added or normal fibroblasts there was hardly any change in the viable cell count.

The above results suggest that a drug supported on a VA-bound carrier exhibits a CAF-specific growth inhibitory activity.

EXAMPLE 9

Examination of Efficiency of Incorporating VA-Lip-DNR into Cancer Cells

Chamber slides (Falcon) were seeded with human fibrosarcoma-derived cell lines HT-1080, HS913T, and Sw684, human breast cancer-derived cell line MCF7, human osteosarcoma-derived cell line Saos2 (all purchased from ATCC), and human hepatic cancer-derived cell line Huh7 (purchased from JCRB Cell Bank) at a cell density of 1×10$^4$ cells/well, cultured overnight, and washed with 10% FBS-containing DMEM. Subsequently, 5 μg/ml (8.85 μM as daunorubicin, 89.25 μM as liposome) of lip-DNR (DaunoXome®) or 5 μg/mL of the VA-lip-DNR (containing 178.5 μM of retinol) obtained in Example 6 was added thereto, the cells were washed 15 minutes and/or 30 minutes after the addition, and fixed by 4% formaldehyde. After washing with PBS, sealing was carried out with Prolong Gold (Invitrogen), and localization of DNR was examined by a fluorescence microscope.

Figure 16:
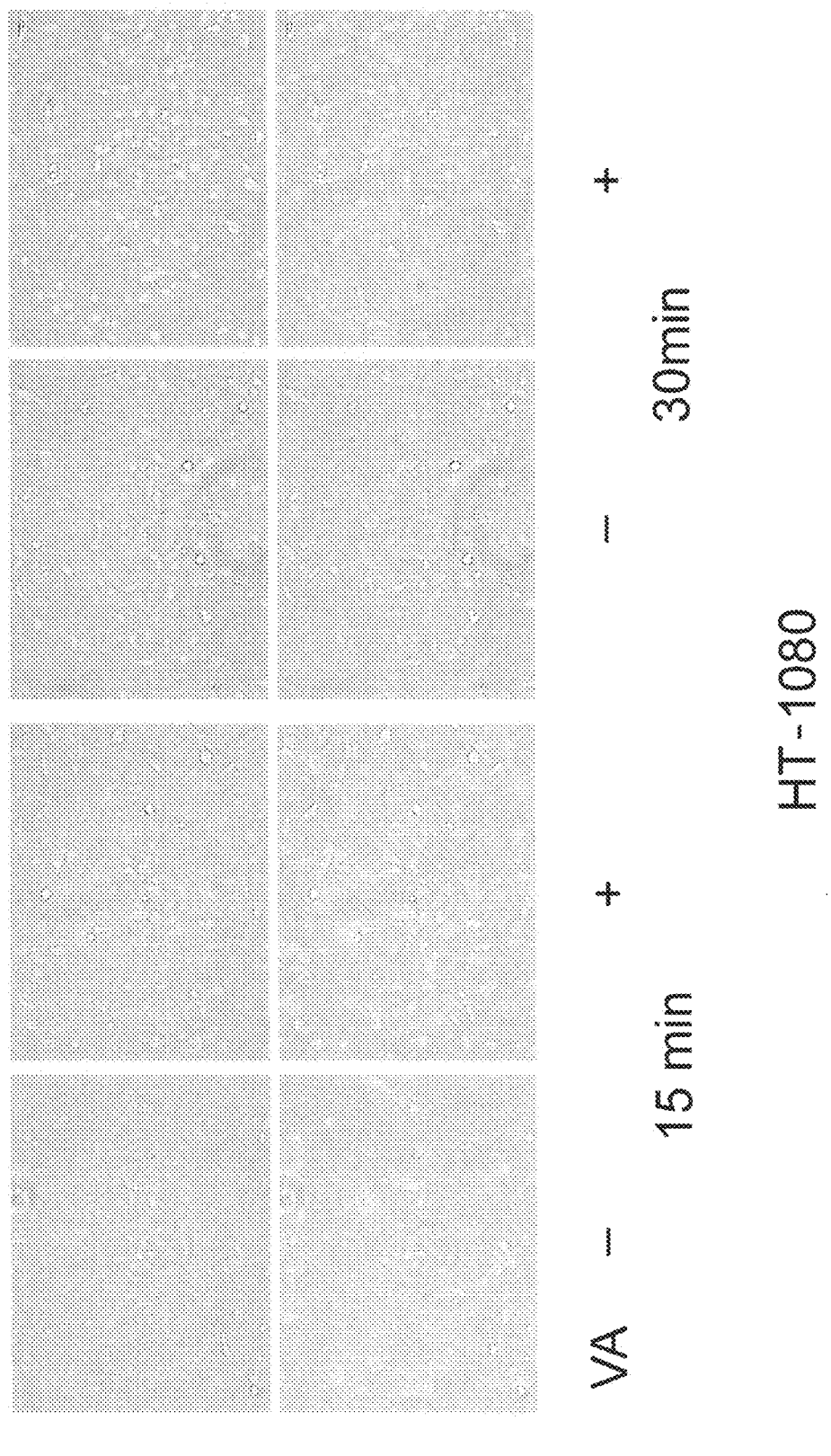
FIG. 16 is a photographic diagram showing the intracellular localization state of liposomal DNR (VA−) or VA-bound liposomal DNR (VA+) in the human fibrosarcoma-derived cell line HT-1080. The upper section shows the localization of DNR, the lower section shows cells that have been subjected to nuclear staining with DAPI, and the figures show the time after addition.
Figure 17:
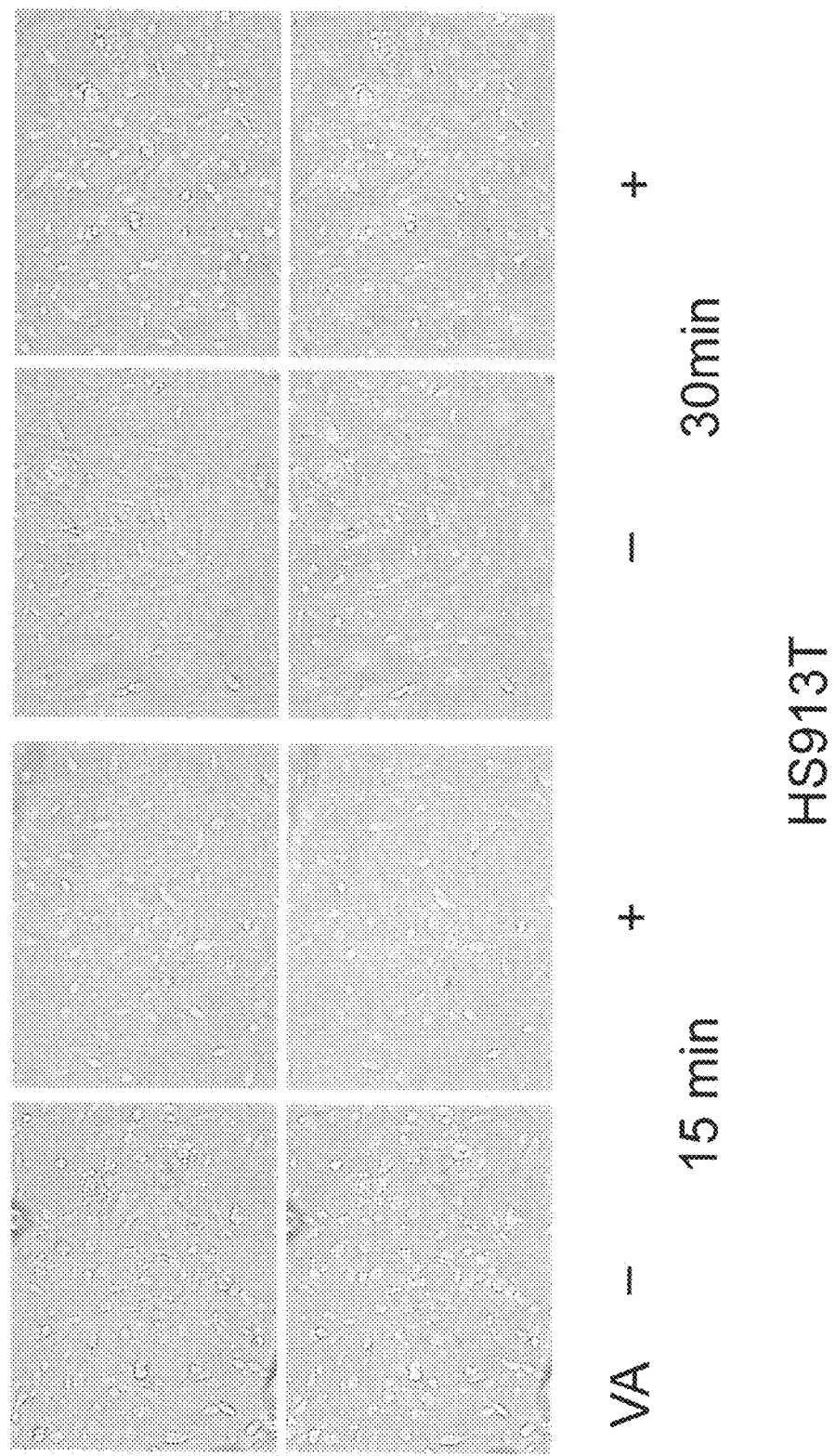
FIG. 17 is a photographic diagram showing the intracellular localization state of liposomal DNR (VA−) or VA-bound liposomal DNR (VA+) in the human fibrosarcoma-derived cell line HS913T. The upper section shows the localization of DNR, the lower section shows cells that have been subjected to nuclear staining with DAPI, and the figures show the time after addition.
Figure 18:
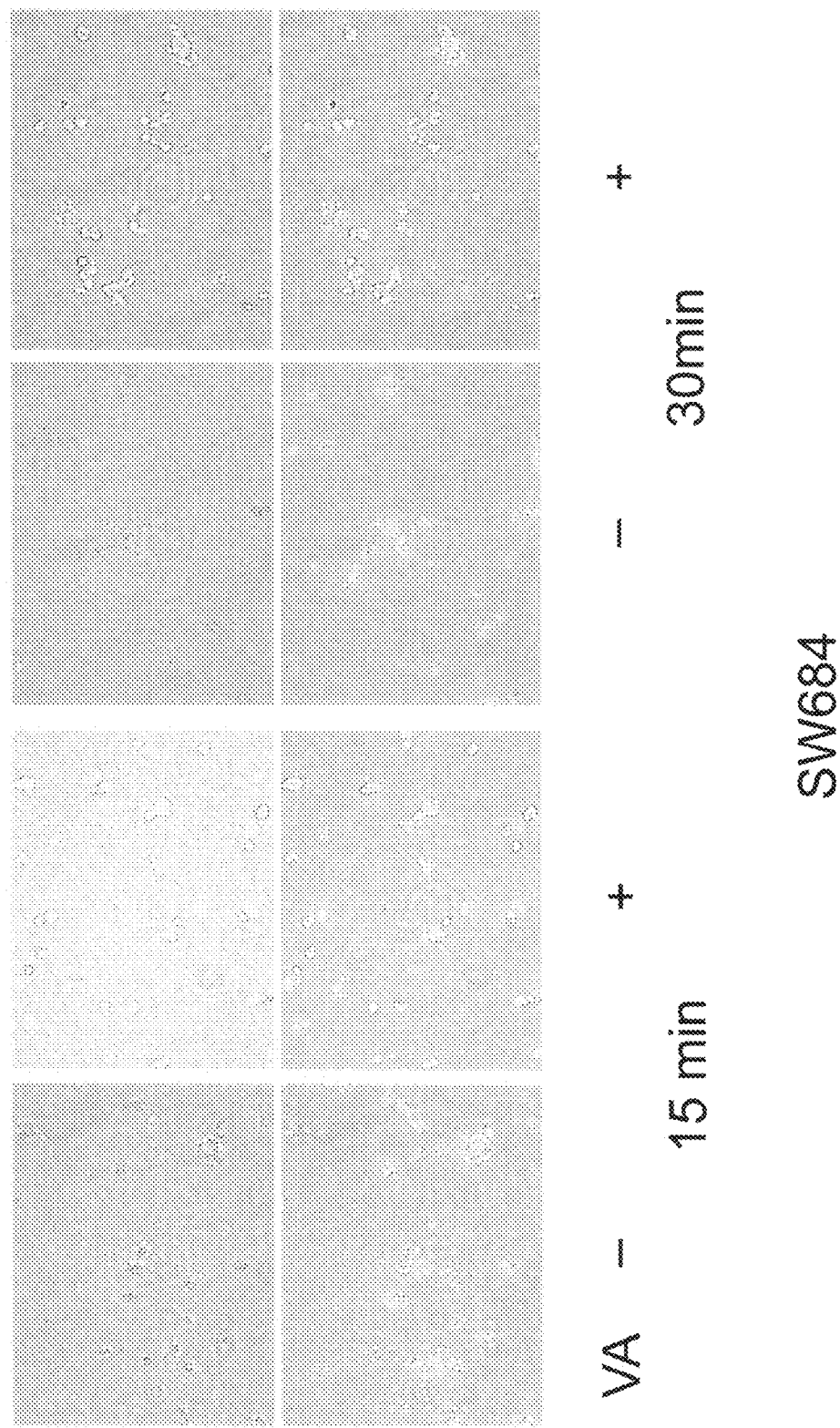
FIG. 18 is a photographic diagram showing the intracellular localization state of liposomal DNR (VA−) or VA-bound liposomal DNR (VA+) in the human fibrosarcoma-derived cell line Sw684. The upper section shows the localization of DNR, the lower section shows cells that have been subjected to nuclear staining with DAPI, and the figures show the time after addition.
Figure 19:
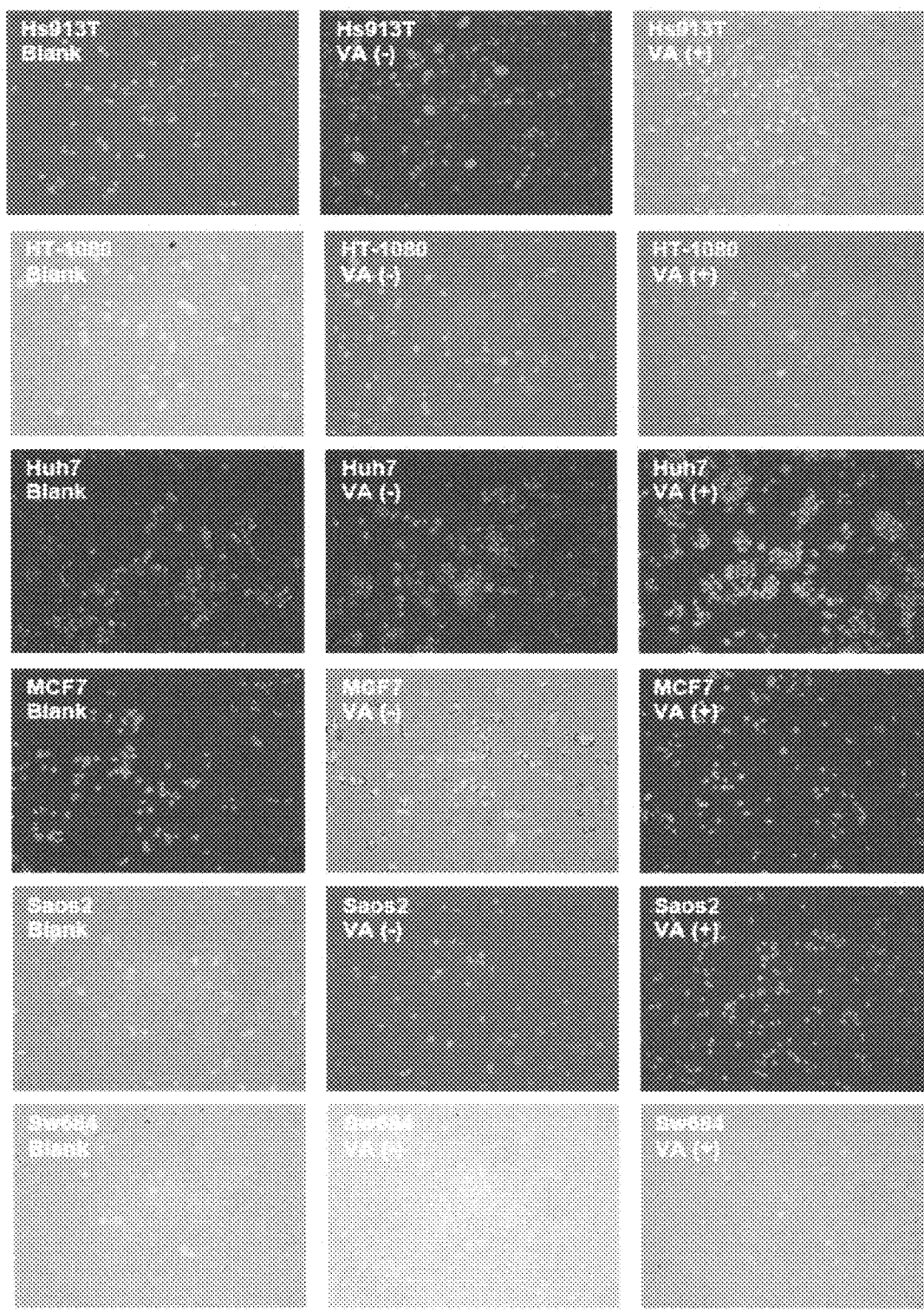
FIG. 19 is a photographic diagram showing the intracellular localization state of liposomal DNR (VA (−)) or VA-bound liposomal DNR (VA (+)) in HT-1080, HS913T, Sw684, Huh7, MCF7, and Saos2 cells (15 min after addition). Blank denotes a microscopic image when neither liposomal DNR or VA-bound liposomal DNR were added.

From the results shown in FIGS. 16 to 18, in all of the cells, in the VA-lip-DNR addition group, DNR, which exhibits a red color under a fluorescence microscope, was localized in the interior of the majority of cells only 15 minutes after the addition, whereas hardly any lip-DNR was incorporated even after 30 minutes had elapsed. This suggests that binding of VA greatly promotes the uptake of liposomal DNR into a cell. Furthermore, from the result shown in FIG. 19, it becomes clear that the above-mentioned promoting effect is observed in various cancer cells, including sarcoma and carcinoma cells.

EXAMPLE 10

Examination of Antitumor Effect of VA-Bound Liposomal Daunorubicin

Figure 20:
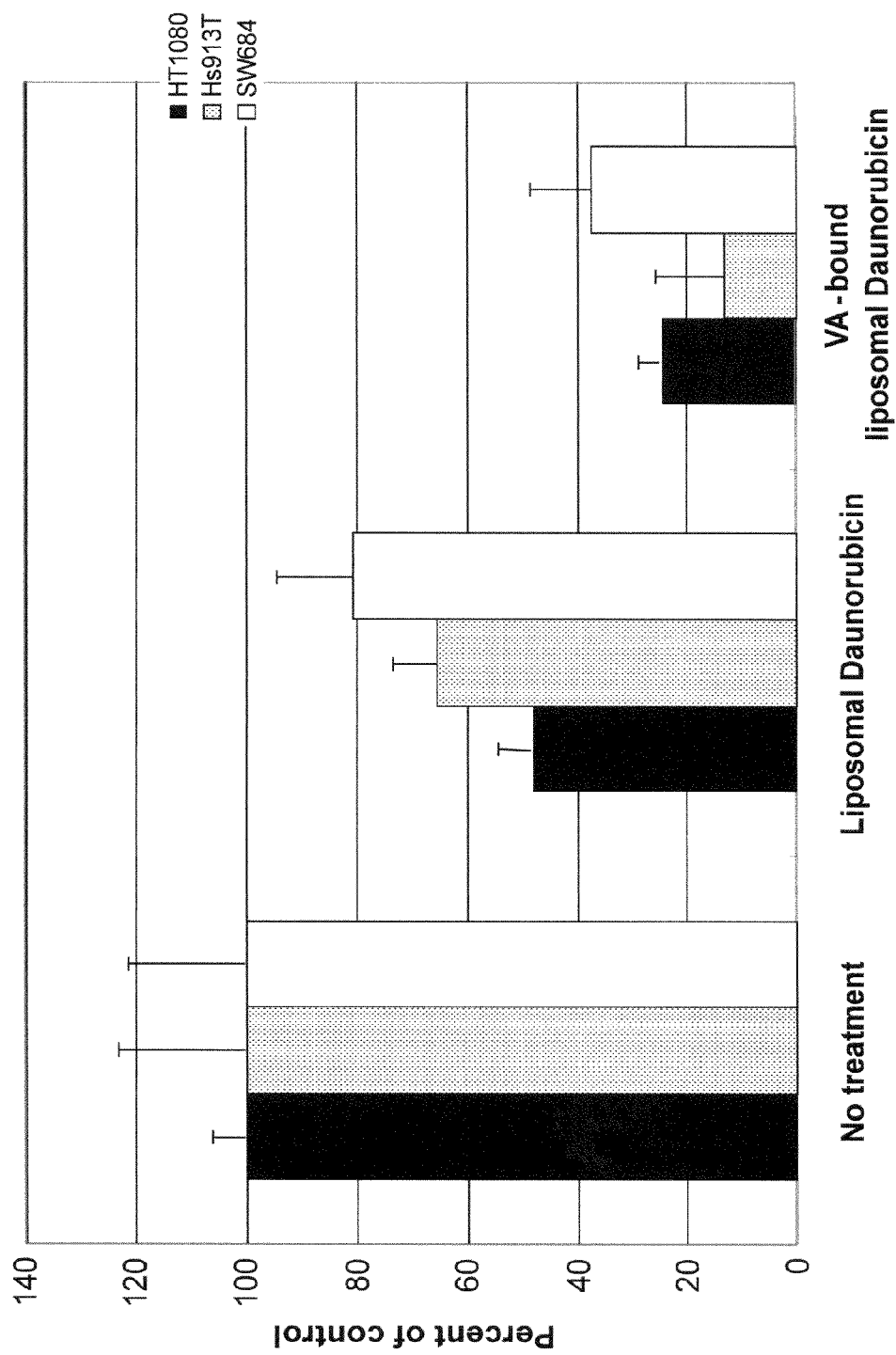
FIG. 20 is a graph of the evaluation of the growth-inhibitory activity of liposomal DNR or VA-bound liposomal DNR toward the human fibrosarcoma-derived cell lines HT-1080, HS913T, and Sw684.

A 96-well plate was seeded with human fibrosarcoma-derived cell lines HT-1080, HS913T, and Sw684 at a cell density of 2×10³ cells/well and cultured overnight, subsequently 5 μg/mL of lip-DNR or 5 μg/mL of the VA-lip-DNR used in Example 6 was added, and culturing was carried out for 15 minutes. Following this, the cells were washed so as to remove drug that was outside the cells, and then cultured with 10% FBS-containing DMEM for 22 hours. 2 hours after WST-1 Cell Proliferation Assay Kit (Cayman Chemical) was added thereto, the absorbance was measured, and the proportion relative to the number of cells when the treatment was not carried out was calculated. From the result shown in FIG. 20, it can be seen that the binding of VA remarkably increases the antitumor activity of liposomal DNR.

EXAMPLE 11

In Vivo CAF-Specific Delivery

Figure 22:
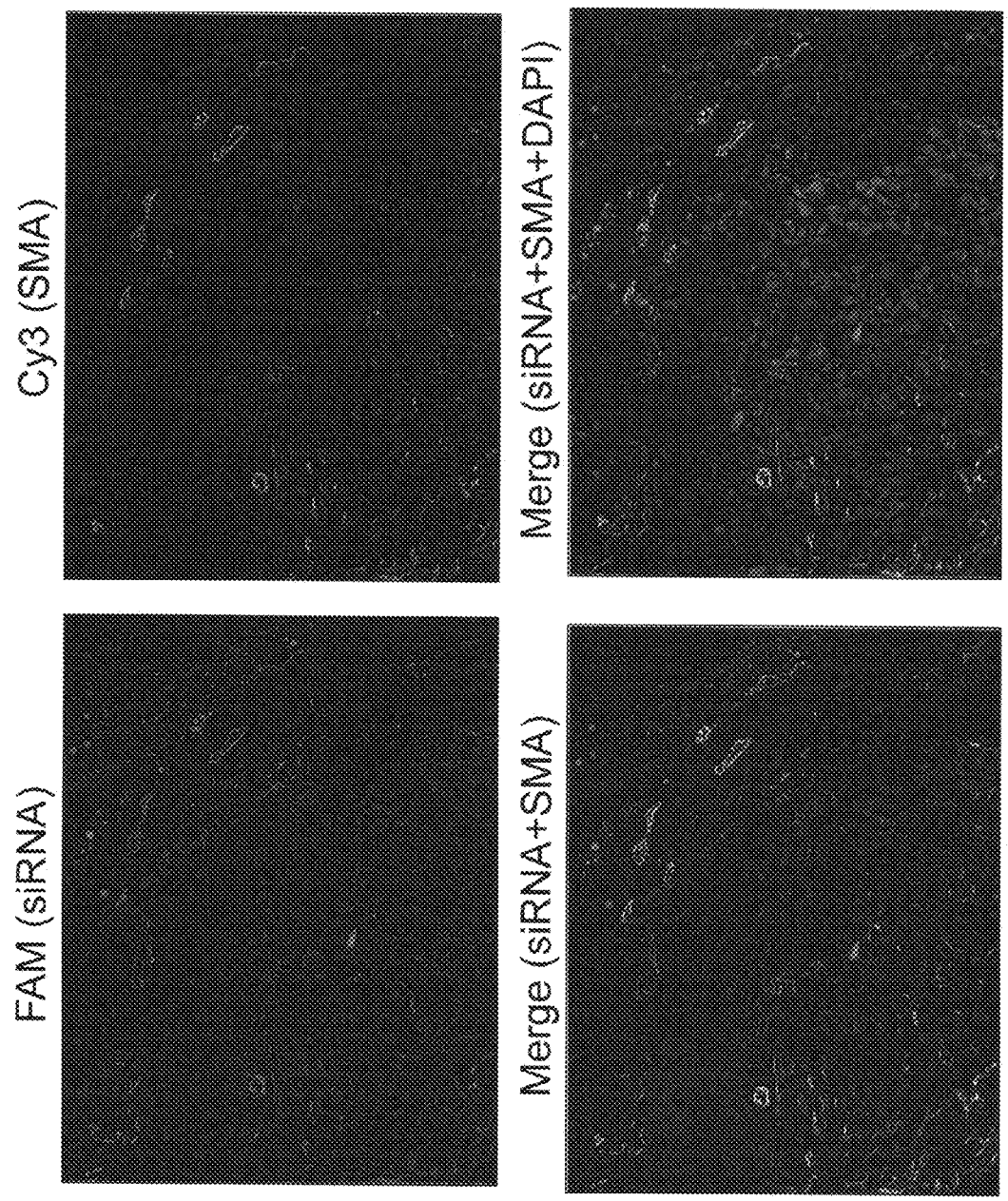
FIG. 22 is a photographic diagram showing the localization of siRNA in the tumor tissue of a tumor-bearing mouse to which VA-lip-siRNA had been intravenously administered. The upper left shows an FAM image, the upper right shows a Cy3 image, the lower left shows a merged FAM and Cy3 image, and the lower right shows a merged FAM, Cy3, and DAPI image. The magnification is 200 times.

NOD-scid mice (6 weeks old, female, n=8, purchased from Sankyo Labo Service Corporation) were subcutaneously inoculated with stomach cancer cell line KATO-III at 2×10⁶ cells, thus making tumor-bearing mice. On the 28th day after inoculation, VA-bound liposome (VA-lip-siRNA-FAM) or liposome containing no VA (lip-siRNA-FAM) used in Example 5 were administered via the tail vein at doses of 200 nmol of VA, 100 nmol of lip, and 100 μg of siRNA. In this VA-bound liposome, part of the VA was already exposed on the surface of liposome when administered. 24 hours after administration, tumor tissue was collected, a tissue specimen was prepared, this was stained with DAPI (Molecular Probe) and Cy3-labeled anti α-SMA antibody, and the localization of siRNA was analyzed. The results are shown in FIGS. 21 and 22.

As is clear from FIG. 21, in the liposome containing no VA, in spite of the presence of CAFs in the tissue shown by the red color due to Cy3, there was hardly any siRNA shown by the green color due to FAM, whereas in the VA-bound liposome, colocalization of CAF and siRNA was observed.

EXAMPLE 12

In Vivo VA-Lip-DNR Antitumor Activity

Figure 23:
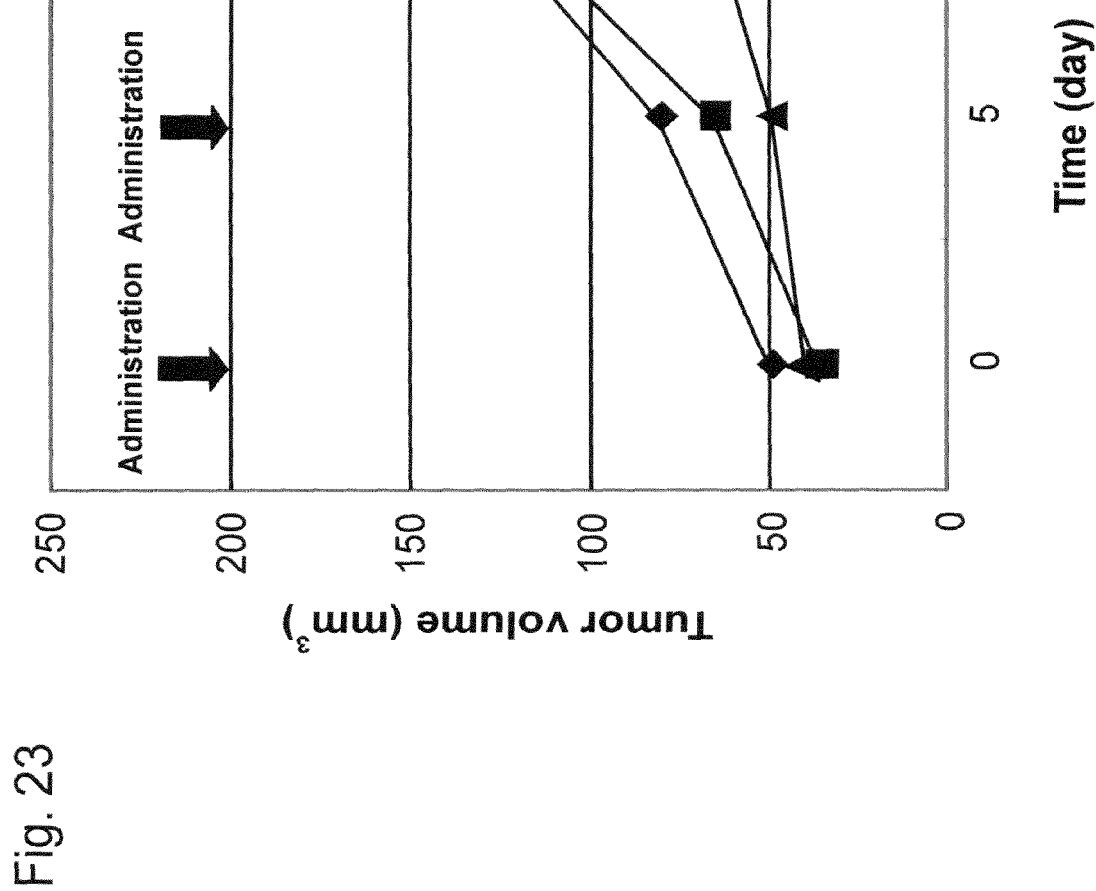
FIG. 23 is a graph showing the results of evaluating the in vivo antitumor activity of VA-lip-DNR (administered twice a week). The ordinate denotes the tumor mass volume (mm$^3$), and the abscissa denotes the number of days after starting the treatment.

Nude mice (6 weeks old, female, n=10, purchased from Sankyo Labo Service Corporation) were subcutaneously inoculated with colon cancer cell line M7609 cells at 2×10⁶ cells, thus giving tumor-bearing mice. From the 14th day after inoculation, VA-lip-DNR or lip-DNR was administered via the tail vein twice a week at a dose 1/40 (0.05 μg per g weight of the mouse) of the normal anticancer administration amount of DaunoXome®. In this VA-lip-DNR, part of the VA was already exposed on the surface of liposome when administered. The change in volume of the tumor after starting administration is shown in FIG. 23. It can be seen from this figure that the drug supported on the VA-bound carrier remarkably suppressed the growth of the tumor.

The above results show that the composition of the present invention is extremely effective in treatment of a cancer.

The invention claimed is:

1. A method for treating a cancer comprising administering an effective amount of an anticancer composition comprising a substance delivery carrier including a targeting agent to a cell selected from the group consisting of a cancer cell and a cancer associated fibroblast, the targeting agent comprising a retinoid, and a drug controlling the activity and growth of a cell selected from the group consisting of a cancer cell and a cancer associated fibroblast to a subject that requires it, wherein the targeting agent is at least partially exposed on the exterior of the carrier before the carrier reaches the cancer cell and/or the cancer associated fibroblast.

2. The method according to claim 1, wherein the retinoid comprises retinol.

3. The method according to claim 1, wherein the drug that controls the activity or growth of a cell is an anticancer agent.

4. The method according to claim 1, wherein the drug that controls the activity or growth of a cell is selected from the group consisting of an inhibitor of activity or production of a bioactive substance selected from the group consisting of TGF-β, HGF, PDGF, VEGF, IGF, MMP, FGF, uPA, cathepsin, and SDF-1, a cell activity suppressor, a growth inhibitor, an apoptosis inducer, and an siRNA, ribozyme, antisense nucleic acid, DNA/RNA chimeric polynucleotide, or vector expressing same that targets one or more molecules from among an extracellular matrix constituent molecule produced by cancer-associated fibroblasts and a molecule involved in the production or secretion of the extracellular matrix constituent molecule.

5. The method according to claim 4, wherein the molecule involved in the production or secretion of the extracellular matrix constituent molecule is HSP47.

* * * * *

UNITED STATES PATENT AND TRADEMARK OFFICE
CERTIFICATE OF CORRECTION

PATENT NO.         : 8,686,052 B2                                              Page 1 of 1
APPLICATION NO.    : 12/450571
DATED              : April 1, 2014
INVENTOR(S)        : Niitsu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1033 days.

Signed and Sealed this

Twenty-ninth Day of September, 2015

Michelle K. Lee
*Director of the United States Patent and Trademark Office*